(12) United States Patent
Caldwell et al.

(10) Patent No.: US 6,312,523 B1
(45) Date of Patent: Nov. 6, 2001

(54) APPARATUS OF FEEDBACK CONTROL FOR THE PLACEMENT OF A POLYMER COMPOSITION INTO A WEB

(75) Inventors: James Michael Caldwell, Cardiff; George Schmermund, Vista, both of CA (US)

(73) Assignee: Nextec Applications, Inc., Vista, CA (US)

( * ) Notice: Subject to any disclaimer, the term of this patent is extended or adjusted under 35 U.S.C. 154(b) by 0 days.

(21) Appl. No.: 09/406,080

(22) Filed: Sep. 27, 1999

Related U.S. Application Data

(60) Division of application No. 08/962,698, filed on Nov. 3, 1997, now Pat. No. 5,958,137, which is a continuation-in-part of application No. 08/407,191, filed on Mar. 17, 1995, now Pat. No. 5,876,792, which is a continuation-in-part of application No. 08/017,855, filed on Feb. 16, 1993, now Pat. No. 5,418,051, which is a continuation of application No. 07/319,778, filed on Mar. 10, 1989, now Pat. No. 5,004,643, which is a continuation-in-part of application No. 07/167,630, filed on Mar. 14, 1988, now abandoned, and a continuation-in-part of application No. 07/167,643, filed on Mar. 14, 1988, now abandoned, and a continuation-in-part of application No. 07/167,797, filed on Mar. 14, 1988, now abandoned, and a continuation-in-part of application No. 07/167,869, filed on Mar. 14, 1988, now abandoned.

(51) Int. Cl.$^7$ ...................................................... B05C 5/02
(52) U.S. Cl. ....................... 118/663; 118/664; 118/665; 118/683; 118/688; 118/712; 118/33; 118/67; 118/68; 118/123; 118/304; 118/643
(58) Field of Search ............................. 118/663–665, 683, 118/688, 712, 33, 67, 68, 123, 304, 643; 427/299, 314, 323, 324, 356, 372.2; 68/200

(56) References Cited

U.S. PATENT DOCUMENTS

| 162,332 | 4/1875 | Allen . |
| 1,281,728 | 10/1918 | Weinheim . |

(List continued on next page.)

FOREIGN PATENT DOCUMENTS

| 57-149559 | 9/1982 | (JP) . |
| 422469 | 9/1974 | (SU) . |
| 89/08553 | 9/1989 | (WO) . |
| 89/08554 | 9/1989 | (WO) . |
| 89/08555 | 9/1989 | (WO) . |

OTHER PUBLICATIONS

"Silicones", Encyl. of Polymer Sci, and Engineering, 2nd ed., Wiley, New York, v.15 (1985–90).

le;.5qCaldwell et al., "Vapor–Permeable, Water–Resistant Fabrics," American Dyestuff Reporter, No. 3, pp. 25–29 (Jan. 30, 1967).

*Primary Examiner*—Laura Edwards
(74) *Attorney, Agent, or Firm*—Lyon & Lyon LLP

(57) ABSTRACT

The present invention relates to methods and apparatus for the controlled placement of a shear-thinnable polymer composition into a moving web. The controlled placement is preferably performed by applying the polymer composition onto a surface of a moving web, shear thinning the composition and placing it into the web, and curing the polymer composition. A preferred apparatus includes one or more process heads that has mounted thereto a rigid knife blade for engagement with the moving web. The knife blade is movable vertically and rotationally. The process head is also movable horizontally along the path of the moving web. A plurality of macro and micro tension zones are established and are monitored for controlling the apparatus and process. Additional measurements of web density, micro porosity, placement of an internal layer of polymer within the web, analysis of elements on the treated web, and the size of the polymer bead applied to the moving web are measured for controlling online the apparatus and the process of this invention. This method and apparatus produces webs that either has some of its structural elements encapsulated by the polymer composition while at least some of the interstitial spaces of the web are open; or has an internal layer extending through the web in a direction generally spaced from at least one major surface thereof; or has both encapsulated structural elements and an internal layer of polymer composition.

27 Claims, 9 Drawing Sheets

U.S. PATENT DOCUMENTS

| | | |
|---|---|---|
| 2,117,432 | 5/1938 | Linscott . |
| 2,575,577 | 11/1951 | Beauchamp . |
| 2,626,941 | 1/1953 | Ilabeck . |
| 2,673,823 | 3/1954 | Biefeld . |
| 2,759,900 | 8/1956 | Caldwell et al. . |
| 2,773,050 | 12/1956 | Caldwell et al. . |
| 2,839,479 | 6/1958 | Caldwell et al. . |
| 2,865,790 | 12/1958 | Baer . |
| 2,893,962 | 7/1959 | Bartell . |
| 2,956,884 | 10/1960 | Caldwell et al. . |
| 2,976,182 | 3/1961 | Caldwell et al. . |
| 3,026,293 | 3/1962 | Caldwell et al. . |
| 3,068,836 * | 12/1962 | Spencer ................................ 118/68 |
| 3,165,423 | 1/1965 | Caldwell et al. . |
| 3,184,421 | 5/1965 | Caldwell et al. . |
| 3,265,529 | 8/1966 | Caldwell et al. . |
| 3,326,713 | 6/1967 | Smith et al. . |
| 3,328,661 | 6/1967 | Grebe . |
| 3,356,628 | 12/1967 | Smith et al. . |
| 3,360,394 | 12/1967 | Griffin et al. . |
| 3,393,186 | 7/1968 | Groves . |
| 3,398,182 | 8/1968 | Guenthner et al. . |
| 3,436,366 | 4/1969 | Modic . |
| 3,594,213 | 7/1971 | Rudman . |
| 3,639,155 | 2/1972 | Hartieim et al. . |
| 3,762,364 * | 10/1973 | Funsch et al. ......................... 118/33 |
| 3,896,251 | 7/1975 | Landucci . |
| 4,032,502 | 6/1977 | Lee et al. . |
| 4,108,825 | 8/1978 | Hayes . |
| 4,110,392 | 8/1978 | Yamazaki . |
| 4,112,179 | 9/1978 | Maccalous et al. . |
| 4,162,243 | 7/1979 | Lee et al. . |
| 4,162,356 | 7/1979 | Grenoble . |
| 4,216,252 | 8/1980 | Moeller . |
| 4,216,290 | 8/1980 | De Beul et al. . |
| 4,250,075 | 2/1981 | Monroe et al. . |
| 4,287,261 | 9/1981 | West et al. . |
| 4,293,611 | 10/1981 | Martin . |
| 4,297,265 | 10/1981 | Olsen . |
| 4,311,760 | 1/1982 | Kalinowski et al. . |
| 4,329,274 | 5/1982 | Faltynek . |
| 4,369,231 | 1/1983 | West et al. . |
| 4,370,365 | 1/1983 | Takamizawa et al. . |
| 4,426,476 | 1/1984 | Chang . |
| 4,427,801 | 1/1984 | Sweet . |
| 4,442,060 | 4/1984 | Bouverot et al. . |
| 4,454,191 | 6/1984 | von Blucher et al. . |
| 4,472,470 | 9/1984 | Modic . |
| 4,478,895 | 10/1984 | Makami et al. . |
| 4,500,584 | 2/1985 | Modic . |
| 4,500,659 | 2/1985 | Kroupa et al. . |
| 4,504,549 | 3/1985 | Pines et al. . |
| 4,539,930 | 9/1985 | Stuck et al. . |
| 4,548,859 | 10/1985 | Kline et al. . |
| 4,555,811 | 12/1985 | Shimalla . |
| 4,560,611 | 12/1985 | Naka et al. . |
| 4,562,219 | 12/1985 | Frye . |
| 4,585,830 | 4/1986 | Sweet . |
| 4,588,614 | 5/1986 | Lauchenauer . |
| 4,600,436 | 7/1986 | Travor et al. . |
| 4,619,864 | 10/1986 | Hendrix et al. . |
| 4,666,765 | 5/1987 | Caldwell et al. . |
| 4,684,570 | 8/1987 | Malaney . |
| 4,753,978 | 6/1988 | Jensen . |
| 4,758,239 | 7/1988 | Yeo et al. . |
| 4,785,047 | 11/1988 | Jensen . |
| 4,828,556 | 5/1989 | Braun et al. . |
| 4,894,105 | 1/1990 | Dyksterhouse et al. . |
| 4,919,739 | 4/1990 | Dyksterhouse et al. . |
| 5,004,643 | 4/1991 | Caldwell . |
| 5,019,062 | 5/1991 | Ryan et al. . |
| 5,102,836 | 4/1992 | Brown et al. . |
| 5,128,198 | 7/1992 | Dyksterhouse et al. . |
| 5,209,965 | 5/1993 | Caldwell . |
| 5,284,677 | 2/1994 | Coughlin . |
| 5,322,727 | 6/1994 | Yankus et al. . |
| 5,322,729 | 6/1994 | Heeter et al. . |
| 5,344,702 | 9/1994 | Haubs et al. . |

\* cited by examiner

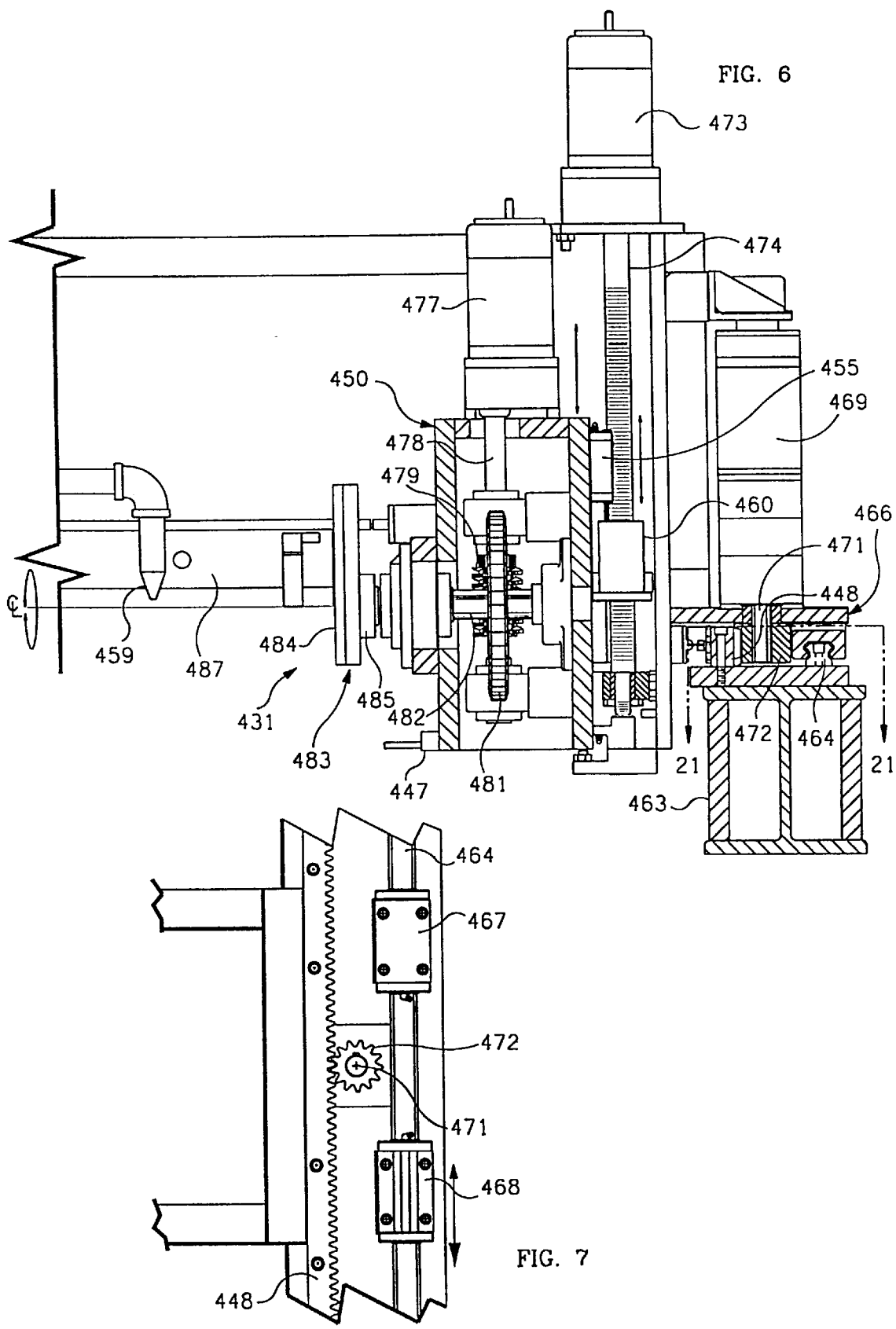

APPARATUS OF FEEDBACK CONTROL FOR THE PLACEMENT OF A POLYMER COMPOSITION INTO A WEB

CROSS-REFERENCE TO RELATED PATENT APPLICATIONS

This application is a division of U.S. patent application Ser. No. 08/962,698 filed on Nov. 3, 1997, now U.S. Pat. No. 5,958,137 issued Sep. 28, 1999; which is a continuation-in-part of U.S. patent application Ser. No. 08/407,191 filed on Mar. 17, 1995, now U.S. Pat. No. 5,876,792 issued Mar. 2, 1999; which is a continuation-in-part of U.S. patent application Ser. No. 08/017,855 filed Feb. 16, 1993, now U.S. Pat. No. 5,418,051 issued May 23, 1995; which is a continuation of U.S. patent application Ser. No. 07/319,778 filed Mar. 10, 1989, now U.S. Pat. No. 5,004,643 issued Apr. 2, 1991; which is a continuation-in-part of U.S. patent application Ser. Nos. 07/167,630, 07/167,643, 07/167,797, and 07/167,869, all filed on Mar. 14, 1988, all now abandoned; and all of which are incorporated herein by reference.

BACKGROUND OF THE INVENTION

1. Field of the Invention

The present invention relates to methods of and apparatus for the introduction of sufficient energy to controllably and selectively place a polymer composition into a porous web. The present invention more particularly relates to methods of and apparatus for the controlled placement of a curable, shear thinning, polymer composition into a web. The controlled placement is preferably performed through the energy controlled viscosity and rheology modified placement of the polymer controlled manner by 1) applying the polymer composition onto a surface of a web, 2) shear thinning the composition and placing it into the web, and 3) curing the polymer composition. This method and apparatus produces a web that either has some of its fibers or structural elements encapsulated by the polymer composition while at least some of the interstitial spaces of the web are open; or has an internal layer extending through the web in a direction generally spaced from at least one major surface thereof; or has both encapsulated structural elements and an internal layer of polymer composition.

2. Description of Related Art

In the prior art, it has been proposed to treat porous webs, especially fabrics, with silicone resins and also with fluorochemicals. Conventional treatments of webs fall into the general categories of (i) surface coatings and (ii) saturations or impregnations.

For example, U.S. Pat. Nos. 3,436,366; 3,639,155; 4,472,470; 4,500,584; and 4,666,765 disclose silicone coated fabrics. Silicone coatings are known to exhibit relative inertness to extreme temperatures of both heat and cold and to be relatively resistant to ozone and ultraviolet light. Also, a silicone coating can selectively exhibit strength enhancement, flame retardancy and/or resistance to soiling. Fluorochemical treatment of webs is known to impart properties, such as soil resistance, grease resistance, and the like.

Prior art fluorochemical and silicone fabric treatment evidently can protect only that side of the fabric upon which they are disposed. Such treatments significantly alter the hand, or tactile feel, of the treated side. Prior silicone fabric coatings typically degrade the tactile finish, or hand, of the fabric and give the coated fabric side a rubberized finish which is not appealing for many fabric uses, particularly garments.

U.S. Pat. No. 4,454,191 describes a waterproof and moisture-conducting fabric coated with a hydrophilic polymer. The polymer is a compressed foam of an acrylic resin modified with polyvinyl chloride or polyurethane and serves as a sort of "sponge", soaking up excess moisture vapor. Other microporous polymeric coatings have been used in prior art attempts to make a garment breathable, yet waterproof.

Various polyorganosiloxane compositions are taught in the prior art that can be used for making coatings that impart water-repellency to fabrics. Typical of such teachings is the process described in U.S. Pat. No. 4,370,365 which describes a water repellent agent comprising, in addition to an organohydrogenpolysiloxane, either one or a combination of linear organopolysiloxanes containing alkene groups, and a resinous organopolysiloxane containing tetrafunctional and monofunctional siloxane units. The resultant mixture is catalyzed for curing and dispersed into an aqueous emulsion. The fabric is dipped in the emulsion and heated. The resultant product is said to have a good "hand" and to possess waterproofness.

This type of treatment for rendering fabrics water repellent without affecting their "feel" is common and well known in the art. However, it has not been shown that polyorganosiloxanes have been coated on fabrics in such a way that both high levels of resistance to water by the fibers/filaments and high levels of permeability to water vapor are achieved. As used herein, the term "high levels of permeability to water vapor" has reference to a value of at least about 500 gms/m$^2$/day, as measured by ASTM E96-80B. Also, as used herein, the term "high level of waterproofness" is defined by selective testing methodologies discussed later in this specification. These methodologies particularly deal with water resistance of fabrics and their component fibers.

Porous webs have been further shown to be surface coated in, for example, U.S. Pat. Nos. 4,478,895; 4,112,179; 4,297,265; 2,893,962; 4,504,549; 3,360,394; 4,293,611; 4,472,470; and 4,666,765. These surface coatings impart various characteristics to the surface of a web, but do not substantially impregnate the web fibers. Such coatings remain on the surface and do not provide a film over the individual internal fibers and/or yarn bundles of the web. In addition, such coatings on the web surface tend to wash away quickly.

U.S. Pat. No. 4,619,864 describes a coating designed to lower the air permeability of the treated web by filling the voids of the web. U.S. Pat. No. 5,322,729 teaches coating a fabric and blowing holes through the coating resin to increase the air permeability.

Prior art treatments of webs by saturation or impregnation also suffer from limitations. Saturation, such as accomplished by padbath immersion, or the like, is capable of producing variable concentrations of a given saturant chemical.

To treat a flexible web, by heavy saturation or impregnation with a polymer material, such as a silicone resin, the prior art has suggested immersion of the flexible web, or fabric, in a padbath, or the like, using a low viscosity liquid silicone resin so that the low viscosity liquid can flow readily into, and be adsorbed or absorbed therewithin. The silicone resin treated product is typically a rubberized web, or fabric, that is very heavily impregnated with silicone. Such a treated web is substantially devoid of its original tactile and visual properties, and instead has the characteristic rubbery properties of a cured silicone polymer.

U.S. Pat. No. 2,673,823 teaches impregnating a polymer into the interstices of a fabric and thus fully filling the interstices. This patent provides no control of the saturation of the fabric. It teaches full saturation of the interstices of the fabric. U.S. Pat. Nos. 4,894,105; 4,919,739; and 5,128,198 teach an immersion of the web into a bath of suspended thermoplastic polymer. Such a treatment provides no control over the placement of the polymer and is capable of producing variable concentrations of a given saturant chemical.

The prior art application of liquid or paste compositions to textiles for purposes of saturation and/or impregnation is typically accomplished by an immersion process. Particularly for flexible webs, including fabric, an immersion application of a liquid or paste composition to the web is achieved, for example, by the so-called padding process wherein a fabric material is passed first through a bath and subsequently through squeeze rollers in the process sometimes called single-dip, single-nip padding. Alternatively, for example, the fabric can be passed between squeeze rollers, the bottom one of which carries the liquid or paste composition in a process sometimes called double-dip or double-nip padding.

Prior art treatment of webs that force a composition into the spaces of the web while maintaining some breathability have relied on using low viscosity compositions or solvents to aid in the flow of the composition. U.S. Pat. No. 3,594,213 describes a process for impregnating or coating fabrics with liquified compositions to create a breathable fabric. U.S. Pat. No. 4,287,261 describes a process for impregnating or coating fabrics with liquified compositions using a siloxane composition having a viscosity in the range of 20,000 to 40,000 centipoise at 25° C. These patents impart no energy into the composition to liquify it while forcing it into the spaces of the web. The composition is substantially liquified before placement onto and into the web. U.S. Pat. No. 4,588,614 teaches a method for incorporating an active agent into a porous substrate. This patent utilizes a solvent to aid in the incorporation of the active agent into the web.

Prior art apparatus for the coating of webs, including fabrics, generally deposits a coating onto the fabric at a desired thickness. Coating at a predetermined thickness can be achieved by deposition of coating material or by the scraping of a coating upon the fabric by knives. Flexible webs are generally urged between oppositely disposed surfaces, one of which would be a doctoring blade or drag knife. The blade or knife smooth the coating and maintain the thickness of the coating to a desired thickness. For example, it is possible to apply a relatively thick silicone liquid elastomer coating to a rough web, typically of fiberglass, in order to make architectural fabric as is taught in U.S. Pat. No. 4,666,765. In this example, the drag knives are set to a thickness of about 2 to 10 mils thicker than the web thickness. This setting, depending on the coating speed, can yield a base coat thickness of approximately 3 to 12 mils thicker than the web thickness.

U.S. Pat. No. 5,480,085 teaches the control of tension between variable speed driver rollers.

Various types of coatings, and various coating thicknesses, are possible. However, a general principle of coating machinery is that the coating material is swept, or dragged, along the surface of the fabric. No special attention is normally given to any pressured forcing of the coating into the fabric, therein making the coating also serve as an impregnant. Of course, some coating will be urged into surface regions of the fabric by the coating process. Generally, however, application of high transversely exerted (against a fiber or web surface) forces at the location of the coating deposition and/or smoothing is not desired in the prior art processes because it is the goal of the prior art coating processes to leave a definite thickness of coating material upon a surface of the fabric, and not to scrape the fabric clean of surface-located coating material.

One prior art silicone resin composition is taught by U.S. Pat. Nos. 4,472,470 and 4,500,584, and includes a vinyl terminated polysiloxane, typically one having a viscosity of up to about 2,000,000 centipoises at 25° C., and a resinous organosiloxane polymer. The composition further includes a platinum catalyst, and an organohydrogenpolysiloxane crosslinking agent, and is typically liquid. Such composition is curable at temperatures ranging from room temperature to 100° C. or higher depending upon such variables as the amount of platinum catalyst present in the composition, and the time and the temperature allowed for curing.

Such compositions may additionally include fillers, including finely divided inorganic fillers. Silicone resin compositions that are free of any fillers are generally transparent or translucent, whereas silicone resin compositions containing fillers are translucent or opaque depending upon the particular filler employed. Cured silicone resin compositions are variously more resinous, or hard, dependent upon such variables as the ratio of resinous copolymer to vinyl terminated polysiloxane, the viscosity of the polysiloxane, and the like.

Curing (including polymerization and controlled crosslinking) can encompass the same reactions. However, in the fabric finishing arts, such terms can be used to identify different phenomena. Thus, controllable and controlled curing, which is taught by the prior art, may not be the same as control of crosslinking. In the fabric finishing arts, curing is a process by which resins or plastics are set in or on textile materials, usually by heating. Controlled crosslinking may be considered to be a separate chemical reaction from curing in the fabric finishing arts. Controlled crosslinking can occur between substances that are already cured. Controlled crosslinking can stabilize fibers, such as cellulosic fibers through chemical reaction with certain compounds applied thereto. Controlled crosslinking can improve mechanical factors such as wrinkle performance and can significantly improve and control the hand and drape of the web. Polymerization can refer to polymer formation or polymer growth.

SUMMARY OF THE INVENTION

The present invention includes methods and apparatus for controlling a porous web under tension, for applying a curable or semi-curable, shear thinnable polymer composition onto the surface of the web, for shear thinning the polymer composition, and placing it into the web to position the polymer within the web in a certain manner, and for partially or fully curing the polymer composition. The methods and apparatus of this invention control the placement of the composition into the web to either encapsulate the structural elements (i.e., the fibers or filaments) making up the web leaving at least some of the interstitial spaces open or providing an internal layer of polymer between the upper and lower surfaces of the web, or some combination of the foregoing.

The methods and apparatus of the present invention permits the application of the polymeric composition onto the surface of the web by a variety of means. After the polymer is applied to the surface of the web, the polymer composition is preferably immediately shear thinned to controllably and significantly reduce its viscosity and place it into selected places within the web. To aid in this process, the web is preferably distorted, typically by stretching at the location of the shear thinning. This distortion facilitates the entrance of the polymer composition into the web by creating a double or dual shear thinning. In the case of the web, this is produced by the combination of the edge condition of the blade, the engineered shear thinnable polymer, the speed of the web, and the subsequent repositioning of the fibers and filaments after their immediate passage under the edge of the blade.

Controlled placement of the polymer composition within a web may be performed by a basic embodiment of a machine in accordance with the present invention, that is as simple as an applicator to apply viscous polymer to the surface of the web, a pair of facilities for applying tension to a section of the web and a blade forced against the web in the section under tension. The web is pulled under tension past the blade, or, alternatively, the blade is moved relative to the web, and the forces generated by the blade cause the polymer composition to flow into the three-dimensional matrix of the web, and controllably be extracted out of the web leaving a thin film of polymer encapsulating selected fibers, or an internal layer of polymer, or both. Tension on the web is preferably released thereafter, and the web is cured.

A preferred apparatus and method disclosed herein includes a supply roll zone, an entry scray drive zone, a processing zone including a plurality of process heads, a curing zone, an exit scray drive zone and a rewind roll zone. Upon entering the processing zone, the moving web is first brushed and vacuumed to clean the surface to be treated. Static electricity is then removed from the web. The web advances through a brake stand under tension past a polymer applicator where a polymer composition is mixed and applied in a controlled manner onto the web adjacent to one of the process heads. Each process head is moveable horizontally along the processing zone to a desired position. Each process head has a blade holding assembly which is vertically and angularly movable to position a knife blade against the moving web at a desired force and angle.

There are primary, secondary, and pre-shearing forces involved in the subject method and apparatus. The primary shear forces occur by the interaction of the blades, polymer composition, and web. The secondary shear forces occur as the web passes through any nip stand or the pull stand, where the fibers or structural elements pop apart as discussed herein. Pre-shearing occurs at a static or dynamic mixer. The mixing device is designed to mix and lower the initial viscosity of the polymer composition prior to application onto the web.

A plurality of idler roll assemblies are provided, typically before and after each process head, to control tension and angle of the web relative to the knife blade. The idler roll assemblies are movable horizontally in the processing zone and are movable vertically, if desired. The web is treated in the processing zone as described hereinafter. As the treated web exits the processing zone it passes through a pull stand. The pull stand operates in conjunction with the brake stand to establish a primary or macro tension zone. Preferably, each roll of the pull stand is independently driven for maximum control of tension as described hereinafter.

The apparatus and method of this invention enables a plurality of tension zones to be established in the processing zone to optimize the treatment of various webs and to enable the manufacture of various products. Tension is monitored in each tension zone and a feedback or quality control loop permits the control of the apparatus in response to the tension measured. Other parameters are also monitored to allow control of the process, including the size of the polymer bead applied, the micro porosity of the web before and after treatment, the placement of the internal layer, the weight add on of the polymer composition, and an analysis of elements present on the web. These measurements are used in the control of the process parameters and adjustments to the apparatus. The treated web is then cured by passing it through a curing zone containing a plurality of ovens or separate heating zones. The first heating zone preferably directs infrared energy at the treated surface of the web. The web is further heated by convection and/or radiant heat to partially or fully cure the web. During the cure the web is supported in a suitable fashion so that no transverse or longitudinal tension is applied to the web so that the web remains in the same state as it is in just after the processing zone. The relaxed state of the web is obtained by transporting the web along a belt, a bed of air, or the like. By allowing the web to remain in a relaxed state, there is no adverse affect to (a) the thin film encapsulation of the individual fibers and filaments, (b) the controlled placement of the internal coating, and (c) the controlled placement of additives in (a) and (b). Preferably, a non-conductive, heat resistant, open mesh belt, made out of Kevlar® is used to transport the web through the curing zone. Other heat resistant materials could be used to transport the web through the curing zone. The cured web has static electricity removed therefrom and is then wound on a take up roll.

The present invention includes novel methods and apparatus for manufacturing webs, fibers and fabrics that have certain desirable physical qualities such as water resistance, increased durability, and improved barrier qualities by combining the use of encapsulated fibers and filaments and a breathable or controlled pore size internal coating with a controlled surface chemistry modification and the like. Such webs, fibers and fabrics can be used to prepare a wide variety of products including, but not limited to, carpets, specialized clothing, career apparel, bioengineered surfaces for diagnostic applications, and upholstery. By use of the present invention, webs, fibers and fabrics can be manufactured with a wide variety of desired physical characteristics.

Methods and apparatus of the present invention can treat webs or fabrics which are generally flat or planar with great internal precision of the internal placement, by combining the use of encapsulated fibers and filaments and a breathable or controlled pore size internal layer, with a controlled surface chemistry modification. Surface chemistry is controlled by using sufficient web tension and frontal blade energy to dislodge the fluorochemical from the web which is then caused to surface orient and/or bloom. The webs or fabrics can comprise fibers in the form of monofilaments, yarns, staples, or the like. The webs or fabrics can also be comprised of a matrix having open cells or pores therein. The webs or fabrics may be a fabric which is woven or non-woven with fibers that can be of any desired composition. The webs or fabrics will generally be tensionable, but not too weak or elastomeric to be processed in accordance with the teachings of the present invention. Any web that is too weak or elastomeric can be treated in accordance with the subject invention if it is laminated to a support backing of paper, film, such as Mylar, or the like and controllably stretched or not stretched prior to applying the backing, thereby setting the condition under which it is stabilized so that it can be treated in accordance with this invention.

The methods and apparatus of this invention are also applicable to treating discrete sheets or pieces of webs such as papers, film sheets, foam sheets, leather hides, woven and non-woven sheets, and the like. The sheet is fed into the apparatus and stops. It is placed under tension and polymer is applied. Rigid or non-rigid blades are moved across the surface of the sheet to cause the controlled placement of the polymer within the sheet as previously described. A non-rigid blade can be flexible but must have sufficient shearing capability.

Webs treated by the methods and apparatus of the present invention contain a curable or semi-curable polymer or copolymer that may contain monomers that are present as a film, coating, or layer within a web that envelopes or encapsulates at least a portion of the fibers or cell or pore walls of the web. The internal layer is a region generally spaced from the outer surfaces of the web which is substantially continuously filled by the combination of the polymers controllably placed therein and the fibers and filaments of the web in this region. The interstices or open cells in the region of the internal layer are also substantially filled. The outer surfaces of the web are substantially free of any polymer deposits other than the thin film encapsulation of the surface fibers and filaments. However, the web remains breathable and is either water resistant or waterproof. The thickness of the internal layer is generally in the range of 0.01 to 50 microns.

At a microscopic level, a web treated in accordance with the present invention, for example, a fabric, can be regarded as being a complex structure, but generally the internal layer is discernable under microscopic examination as shown in the accompanying scanning electron microscope photographs that will be discussed hereinafter.

Depending upon the conditions used to produce it, a web produced in accordance with the present invention can characteristically and preferably exhibit a soft hand and flexibility that is comparable to the hand and flexibility of the untreated web. In some cases, the difference between the hand and the feel of the treated and untreated webs may not be perceptible, but may be engineered to be altered through the controlled crosslinking of the polymer. This is particularly surprising in view of the substantial amount of polymer being added to the web. A treated web has a breathability which, by a present preference, can approach a high percentage of the untreated web notwithstanding the relatively large amount of polymer present.

A polymer composition having a viscosity in the range of greater than 1,000 centepoise but less than 2,000,000 centepoise is preferably used to produce the treated webs. If desired, additives or modifiers can be admixed with such a composition to adjust and improve properties of such composition or web, such as viscosity and/or rheology, combustibility, reflectivity, flexibility, conductivity, light fastness, mildew resistance, rot resistance, stain resistance, grease resistance, and the like. In general, a web treated in accordance with this invention exhibits enhanced durability. These additives are generally controlled by the engineered shear thinning polymer composition and the method and apparatus of this invention to be oriented and surface exposed on the surface of the thin film on the encapsulated fibers, or on one or both surfaces of the internal layer, or on one or both surfaces of the web, or some combination of the above.

Additives and/or modifiers can be mixed into the polymer composition before, during, and after application of the composition to a porous web. To apply one or more additives after the polymer composition is applied, the additives are sprayed on prior to curing. The application of pressure causes impregnation of the additives into the top or bottom surfaces of the web and into the polymer composition within the web.

A web made by the present invention can preserve much, or even substantially all, of its original untreated hand even after an extended period of use while demonstrating excellent abrasion resistance. In contrast, an untreated web typically loses its original hand and displays reduced abrasion resistance after an extended period of use. This is achieved by the formation of an internal layer that prevents new fiber surfaces from being exposed, thereby minimizing the amount of untreated surfaces that degrade much faster than the treated fibers.

A web treated by this invention can undergo a large number of machine washings with detergent without experiencing appreciable or significant change or deterioration. The polymer matrix composition prolongs the use and service life of a web, usually by at least an order of magnitude, depending on such factors as web type, extent and type of treatment by the teachings of this invention, and the like.

Optionally, and as indicated above, agents or additives carried by the polymer composition into a web can be stably fixed and selectively placed in the web with the cured polymer. For example, agents such as ultraviolet light absorbers, dulling agents, reflectivity enhancers, antimicrobial agents, flame resistant agents, heat absorbant, anti-static agents, and the like, which modify a web's response to light and radiation are desirably located substantially upon the surfaces of the web's fibers. When these agents are incorporated into the enveloping polymer film, it appears that they are retained where they are deposited. A present preference for ultraviolet resistant webs in the practice of this invention is to employ a silicone polymer composition that contains a benzophenone.

In addition, the present invention is directed to methods and apparatus for making polymer encapsulated and internally coated webs. Such methods and apparatus includes means for tensioning a porous, flexible web; means for applying a curable, shear thinnable, polymer composition thereto; and means for applying a localized shear force sufficient to cause the controlled shear thinning of an engineered polymer over and against one or both surfaces of the tensioned web. The shear force is sufficient to shear thin the polymer, to selectively distribute and place the polymer composition within the web as an internal layer in a region extending generally in spaced relationship to the surfaces of the web and to generally envelop surface portions of at least some of the web fibers or form a lining of the cells or pores of the web. The internal layer is not necessarily flat but may undulate or meander through the web, occasionally even touching one or both surfaces of the web. Alternatively, the shear force and other variables are controlled to encapsulate at least some of the internal and external fibers of the web without forming an internal layer. Also, control of the methods and apparatus can result in a treated web having a combination of an internal layer and encapsulation of at least some of the fibers of the web leaving at least some of the interstitial spaces open. The web is then optionally interveningly stored, or is (preferably) immediately subjected to curing conditions (heat, moisture and/or radiation) which converts the polymer composition as deposited in the web into a solid elastomeric polymer. The web can be semi-cured or partially cured and can be finally cured or post cured at a later time.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

BRIEF DESCRIPTION OF THE DRAWINGS

FIG. 6 is a partially cross-sectioned view illustrating the facilities for moving the process head horizontally and for moving the blade holding assemblies vertically and angularly.

FIG. 7 is a cross-sectional view taken along line 7—7 of FIG. 6 illustrating the facilities for moving the process head horizontally in the processing zone.

DESCRIPTION OF THE PREFERRED EMBODIMENTS

Figure 1:
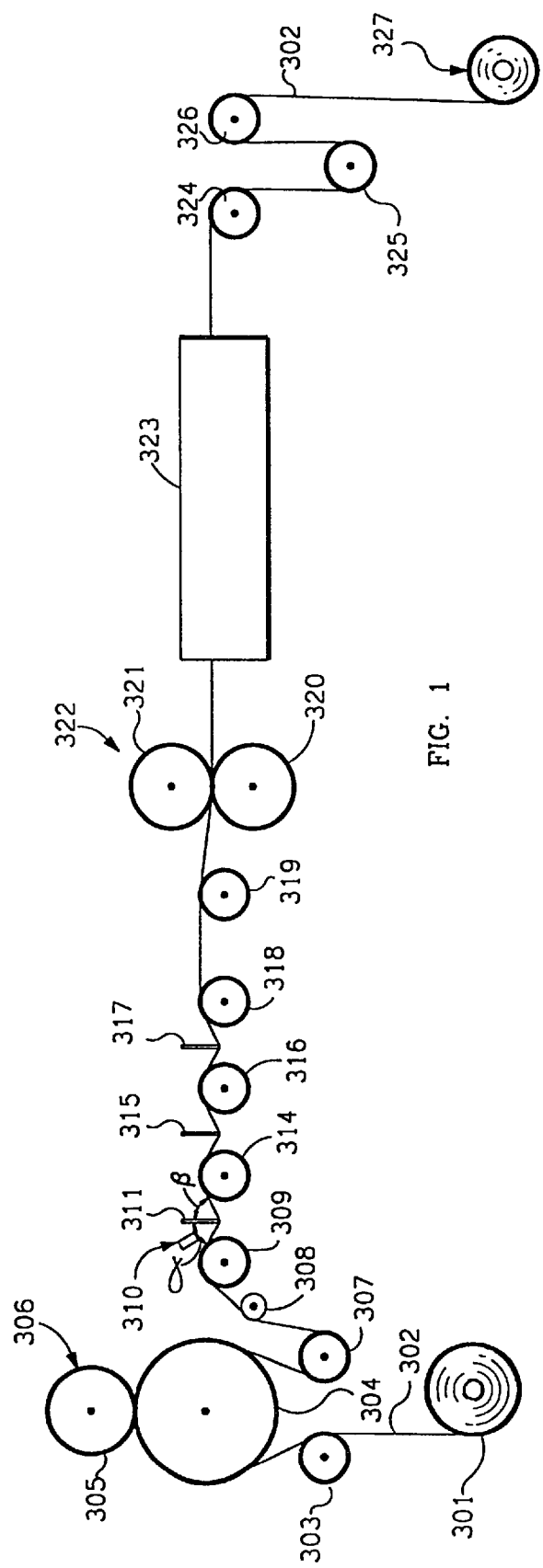
FIG. 1 illustrates diagrammatically one embodiment of a method and apparatus suitable for use in the practice of the present invention.

The following description is of the best presently contemplated mode of carrying out the invention. This description is made for the purpose of illustrating the general principles of the inventions and should not be taken in a limiting sense.

The present invention relates to methods and apparatus for manufacturing a treated web. The subject methods and apparatus involve the control of numerous variables, including, without limitation, web tension (both overall web tension as well as the web tension immediately before and after each individual blade), angle of entry of web into each blade, blade angle in relation to horizonal reference point, blade pressure against moving web, angle of exit of web from each blade, web speed, number of blades, the pressure of the leading nip rolls, the pressure of the trailing nip rolls, static control, thickness of each blade, bevel on each blade, oven cure temperature, oven cure dwell time, blade temperature and blade surfaces and edge conditions and blade finish.

Other variables that affect the finished product, but are not directly related to the methods and apparatus, include, without limitation, the polymer blend, the starting viscosity of the polymer composition, accelerators added to the polymer composition, additives added to the polymer composition, the type of web used, ambient temperature, humidity, airborne contaminants, lint on web, pre-treatment of web, sub-web surface temperature, and web moisture content.

With respect to the blades, the temperature of the blade can be kept cool to keep the polymer composition from curing prematurely. This can be accomplished by passing a coolant through or around the blade or by other means well known in the art. Alternatively, the blade could be heated by passing a heated fluid around or through the blade, if desired to improve or alter the viscosity and rheology for the required changes in the polymer necessary to achieve a specific product.

The blade finish is also important. A hard, smooth surface of both blade face and edges is desirable to shear thin the polymer and keep it flowing and to maximize friction or selectively create shear forces between the web, the polymer, and blade(s). For some applications, the blades should preferably remain rigid in all dimensions and have minimal resonance in order to get uniform web treatment.

The apparatus has facilities for rotating the angle of each blade ±90° from the vertical. In order to vary the shear and placement forces of the blade against the web, polymer and additives, adjustment facilities are provided for moving the blade vertically up and down and moving the blade forward and backward horizontally. All three axis are important for creating the desired control which causes the encapsulated fibers and/or filaments, the additive placement and orientation on the fiber and filaments, the optional internal layer, and the controlled thickness of the encapsulating films or internal layer. The lateral placement of each blade relative to the other is also important and facilities are provided for allowing lateral movement of each blade toward and away from each other. The lateral placement of each blade controls the micro tension and elastic vibration of the web between the preceding roll and the blade, thereby controlling the web after the immediate exit of the web from the blade and controlling the Coanda Effect, as described in U.S. Pat. No. 4,539,930, so that controlled placement of the internal layer takes place.

Changing the tension of the web results in changes internally in the web, such as the position of the internal layer of the web, as well as how much or how little fiber encapsulation occurs, and the thickness of the film encapsulating the individual fibers or filaments.

At the leading edge of the blade, the web is stretched longitudinally and the polymer is simultaneously and dynamically shear thinned, placed into the web, and partially extracted from the web, thereby leaving encapsulated fibers and filaments and/or an internal layer. As the web passes the leading edge of the blade, the elastic recovery forces of the web combined with the relaxation or elastic recovery of the fibers and filaments causes fiber encapsulation and the surface chemistry modification (or bloom). It is believed that this occurs by the popping apart of the individual fibers and filaments. The fibers and filaments either pull the polymer from the interstitial spaces or the rheology of the polymer attracts it to the fibers and filaments or some combination of the two. The end result is that the polymer in the interstitial spaces moves to the fibers and filaments as they move or snap apart, thereby creating encapsulated fibers and filaments. At the bottom surface of the blade, the thickness, depth, and controlled placement of the internal layer is determined. A wider blade results in a thicker internal layer of polymer. Further, the dynamics of stretch and relaxation of the fibers provides for an even energy necessary for the thin film encapsulation of the polymer composition over the fibers.

Passing the treated web through the exit nip rolls pushes the fibers or structural elements of the web together. The hardness of and the material of the exit nip rolls affects the finished web. The exit nip rolls could be either two rubber rolls or two steel rolls, or one steel roll and one rubber roll, and the rubber rolls could be of different durometers. Further, the variation of the hardness of one or both nip rolls changes the contact area or footprint between the nip rolls and the web as the web passes therebetween. With a softer roll there is a larger contact area and the web is capable of retaining the (a) thin film encapsulation of the individual fibers and filaments, (b) the controlled placement of the internal coating, and (c) controlled placement of the additives in (a) and (b). With a harder roll there is a smaller contact area which is appropriate for heavier webs.

Additional controllable variables include the various controls of each blade, the nip rolls durometer, the nip release effect, the nip surface characteristics, the guidance, and the pre-treatment of the substrate. Some of the controllable variables are: 1) web tension, 2) angle of entry of fabric into the blade,3) blade angle in reference to horizontal position, 4) blade pressure against fabric (blade height), 5) angle of exit of fabric from blade, 6) web speed, 7) number of blades, 8) initial rheology and viscosity of polymers, 9) nip pressure, 10) entry nip pressure 11) static control, 12) blade thickness and shape, 13) polymers and polymer blends, 14) accelerators and inhibitors added to polymers, 15) additives in polymers, 16) oven cure temperature, 17) oven cure dwell time, 18) oven supporting means, 19) substrate type, 20) ambient polymer temperature, 21) humidity, 22) degree web is deformed under lateral tension, and 23) airborne contaminants and lint on the web. Control of the above variables affects: (a) the thin film encapsulation of the individual fibers and filaments, (b) the controlled placement of the internal coating, and (c) the controlled placement of the additives in (a) and (b). Further controllable variables are discussed infra with respect to the preferred embodiments of the method and apparatus.

An increase in web tension causes less polymer to be applied to the web, and also, more of what is applied to be extracted from the web. Web tension occurs between the entrance pull stand and the exit pull stand. The primary tension is a result of the differential rate between the driven entrance pull stand and the driven exit pull stand whereby the exit pull stand is driven at a rate faster than the entrance pull stand. Other factors which effect tension are (1) the blade roll diameter, (2) the vertical depth of the blade(s), (3) the durometer of the entrance pull stand roll and rubber roll of the exit pull stand, and (4) the friction as the web passes under the blade(s). The larger the blade roll diameter, the higher the tension of the web. If the drive rate of the web remains constant, then increasing the depth of the blade into the web creates a greater micro tension condition under the blade. Similarly, decreasing the depth into the web decreases the micro tension under the blade. The lower the durometer of the entrance pull stand roll and rubber roll of the exit pull stand, the larger the footprint or contact area between the rolls. A larger footprint produces more surface friction, thereby limiting web slippage and increasing tension. Likewise, web slippage can be effected by changing the surface texture of the rolls, i.e., a smooth roll will allow greater slippage than a highly contrasting or rough surface texture. Increasing friction, as the fabric passes under the blade(s), also produces tension. Friction is a function of the surface area of the bottom of the blade(s). Increasing the surface area increases the friction which increases the tension. Other variables which control tension are described in relation to the preferred embodiment discussed infra.

The entry angle of the web into the blade(s) can be varied by blade roll height, blade roll diameter, blade angle, distance between prior blade roll(s) and blade(s), and height of the blades. Increasing the blade roll height and blade roll diameter increases the entry angle into the blade. Rotating the blade angle clockwise from the perpendicular, with the web running left to right, increases the entry angle. Likewise, rotating the blade angle counter-clockwise from the perpendicular, with the web running left to right, decreases the entry angle. Decreasing the distance between the roll before the blade and the blade decreases the angle of entry. Increasing the downward depth of the blade(s) into the web decreases the angle of entry into the blade(s).

The angle of the blade(s) is completely changeable and fully rotational to 360°. The fully rotational axis provides an opportunity for more than one blade per rotational axis. Therefore, a second blade having a different thickness, bevel, shape, resonance, texture, or material can be mounted. Ideally the apparatus contains two or three blades per blade mount.

The blade height or blade pressure applied against a web can be obtained through the vertical positioning of the blade(s) in the blade mount. The greater the downward depth of the blade(s), the greater the pressure. Blade pressure against the web is also accomplished through the tension of the web as described above.

The same line components that affect the entry angle of the web into the blade(s), also affect the exit angle of the web out of the blade. Any changes in blade roll(s) vertical height, diameter, or distance away from the blade, affects the exit angle of the web. If the angle of the blade is rotated clockwise as described above, the entry angle of the web increases, thus decreasing the exit angle.

Web speed is proportional to the variable speed of the motor which drives the entrance and exit nip stands. Web speed can effect the physics of the polymers as the web passes under the blades.

The number of blades can vary. Generally, more than one blade is required. The polymer is first applied onto the web prior to the first blade. At this blade, a rolling bead of polymer can exist at the interface of the blade and the web (entry angle) Basically, a high viscosity polymer is applied and through the process of shear thinning, the viscosity is greatly decreased, allowing the polymer to enter into the interstitial spaces of the web. Any blade(s) after the first blade, serves to further control the polymer rheology and viscosity and continue the controlled placement of the polymer into the web. This is accomplished by controllably removing excess polymer to obtain an even distribution of polymer to any area, or a combination of the three areas of a) the thin film encapsulation of the individual fibers and filaments, b) the controlled placement of the internal layer, and c) the controlled placement of the additives in a) and b).

The initial process dynamics for the rheology and viscosity of the polymer is designed and engineered with the required attributes to achieve (a) the thin film encapsulation of the individual fibers and filaments, (b) the controlled placement of the internal layer, and (c) the controlled placement of the additives in (a) and (b). If the polymer viscosity is high, the polymer may need to be pre-thinned by using a dynamic mixer or three-roll head. The dynamic mixer or the three-roll head can significantly reduce the viscosity and even pre-place the polymer into a thick substrate or web to allow the blades to further shear thin and enhance the flow and placement of the polymer.

The entrance pull stand is a driven roll proportionally driven at a predetermined rate slower than the exit pull stand. The entrance and exit pull stands are adjustable from about 100 pounds of force to 5 or more tons of force. The bottom rolls of both the entrance and exit pull stands have micro-positioning capability to provide for gap adjustment and alignment. The composition of the top roll of the entrance and exit pull stands is chosen based on the durometer of the urethane or rubber. The top roll of the exit pull stand preferably utilizes a Teflon sleeve which will not react with the polymers used in the process. The bottom roll of the exit pull stand is preferably chrome plated or highly polished steel to reduce the impression into the preplaced polymer in the web.

If desired, non-contact antistatic devices may be installed in locations where noticeable levels of static buildup are detected. However, there is no evidence of adverse effects due to static buildup in the process.

Blade thickness and shape have substantial effects on the movement of the structural elements of the web during processing and more importantly, the viscoelastic flow characteristics of the polymer in controlling (a) the thin film encapsulation of the individual fibers and filaments, (b) the controlled placement of the internal coating, and (c) the controlled placement of the additives in (a) and (b). The blade bevel can effect the entry angle of the web and effect the sharpness of the leading edge of the blade. A sharper leading edge has a greater ability to push the weave or structural elements of the web longitudinally and traversely, increasing the size of the interstitial spaces. As the web passes the leading edge of the blade, the interstitial spaces snap back or contract to their original size. The polymer viscosity is reduced and the polymer is placed into the web at the leading edge of the blade. Blade thickness and shape effects the polymers and their selected additives and the placement thereof. Preferably, the combination of the leading edge condition and the two surfaces (the front and the bottom) that meet at the leading edge are RMS 8 or better in grind and/or polish. This creates a precise leading edge; the more precise the leading edge, the more the shear thinning control.

There are a number of pre-qualifiers or engineered attributes of polymers that enhance control of flow and polymer placement in:(a) the thin film encapsulation of the individual fibers and filaments, (b) the controlled placement of the internal coating, and (c) the controlled placement of the additives in (a) and (b). Blending polymers is one way to achieve ideal flow and placement characteristics. An example of a blended polymer is where one polymer, selected for its physical properties, is mixed with another polymer that is selected for its viscosity altering properties. Many tests using different polymer blends have been done. Polymer blends vary by both chemical and physical adhesion, durability, cure dwell time required, cure temperature required, flexibility, percentage add-on required, performance requirements, and aesthetics.

Accelerators and inhibitors which are added to polymers, generally produce three effects. An illustrative accelerator or inhibitor is a platinum catalyst, which is a cure or crosslinking enhancer. The first effect it produces is to control the time and temperature of the web as it cures. A cure or controlled crosslinking enhancer can significantly assist in controlling the drape and hand feel of the web. The second effect is to to alter the cure to allow the web to reach partial cure and continue curing after leaving an initial heat zone. This second effect also assists in retaining the drape and hand feel of the web. The third effect of inhibitors is to achieve a semi-cure for later staging of the cure.

Additives which are added to the polymers significantly control surface chemistry. Surface chemistry characteristics are controlled by including additives that have both reactive and bio-interactive capabilities. The method and apparatus of this invention can control the placement of the additives on the surface of the thin film encapsulating the fibers, on either or both surfaces of the internal layer, on either or both surfaces of the web, or any combination of the foregoing. Additives and/or modifiers can be mixed into the polymer composition before, during, and after application of the composition to a porous web. To apply one or more additives after the polymer composition is applied, the additives are sprayed on prior to curing. The application of pressure causes impregnation of the additives into the top or bottom surfaces of the web and into the polymer composition within the web.

The oven cure temperature and the source and type of cure energy, are controlled for a number of reasons. The oven cure temperature is controlled to achieve the desired crosslinked state; either partial or full. The source and type of energy can also affect the placement of the polymer and additives. For example, by using a high degree of specific infrared and some convection heat energy for cure, some additives can be staged to migrate and/or bloom to the polymer surfaces.

Oven cure temperature is thermostatically controlled to a predetermined temperature for the web and polymers used. Machine runs of new webs are first tested with hand pulls to determine adhesion, cure temperature, potentials of performance values, drapability, aesthetics, etc. The effect on the web depends on the oven temperature, dwell time and curing rate of the polymer. Webs may expand slightly from the heat.

Oven cure dwell time is the duration of the web in the oven. Oven cure dwell time is determined by the speed of the oven's conveyor and physical length of the oven. If the dwell time and temperature for a particular web is at maximum, then the oven conveyor speed would dictate the speed of the entire process line or the length of the oven would have to be extended in order to increase the dwell time to assure proper final curing of the web.

During the cure the web is supported in a suitable fashion so that no transverse or longitudinal tension is applied to the web so that the web remains in the same state as it is in just after the processing zone. The relaxed state of the web is obtained by transporting the web along a belt, a bed of air, or the like. By allowing the web to remain in a relaxed state, there is no adverse affect to (a) the thin film encapsulation of the individual fibers and filaments, (b) the controlled placement of the internal coating, and (c) the controlled placement of additives in (a) and (b). Preferably, a non-conductive, heat resistant, open mesh belt, made out of Kevlar® is used to transport the web through the curing zone. Other heat resistant materials could be used to transport the web through the curing zone.

The physical construction and chemistry of the web is critical. The amount of control over the rheology of the polymer and the tension on the web are dependent on the physical construction and chemistry. The web selected must have physical characteristics that are compatible with the flow characteristics of the polymer.

The ambient polymer temperature refers to the starting or first staging point to controlling the viscosity and rheology. The process head can control the ambient polymer temperature through temperature controlled polymer delivery and controlled blade temperatures.

Humidity can sometimes inhibit or accelerate curing of the polymer. Therefore, humidity needs to be monitored and, in some conditions, controlled.

The degree the web is deformed under lateral tension is controllable by the choice of the physical construct of the web, the blade angle, the blade leading edge condition, and the micro and macro tension of the web.

Airborne contaminants and lint on the web can affect primability and can create pin holes in the polymer. Therefore, airborne contaminants and lint on the web need to be controlled to reduce or eliminate pin holes or uncontrolled primability.

In view of the fact that between the shear thinning stations and the oven, the polymer composition may begin to set or partially cure, it may be desirable to overshear so that by the time the web gets to the curing oven, it will be at the point where it is desired that the cure occur. This over shear effect is a matter of controlling certain variables, including the force of the blades against the moving web, as well as the tension and speed of the web.

By having a number of shear thinning blades, you create a multiple shear thinning effect, which changes the final construct of the polymer and the (a) thin film encapsulation of the individual fibers and filaments, (b) controlled placement of the internal coating, and (c) controlled placement of the additives in (a) and (b). It is understood that the first shear thinning causes viscoelastic deformation of the polymer composition which, due to its memory, tends to return to a certain level. With each multiple shear thinning, the level to which the polymer starts at that shear point and returns is changed. This is called thixotropic looping or plateauing.

Definitions

The term "web" as used herein is intended to include fabrics and refers to a sheet-like structure (woven or non-woven) comprised of fibers or structural elements. Included with the fibers can be non-fibrous elements, such as particulate fillers, binders, dyes, sizes and the like in amounts that do not substantially affect the porosity or flexibility of the web. While preferably, at least 50 weight percent of a web treated in accordance with the present invention is fibers, more preferred webs have at least about 85 weight percent of their structure as fiber. It is presently preferred that webs be untreated with any sizing agent, coating, or the like, except as taught herein. The web may comprise a laminated film or fabric and a woven or non-woven porous substrate. The web may also be a composite film or a film laminated to a porous substrate or a double layer.

The term "webs" includes flexible and non-flexible porous webs. Webs usable in the practice of this invention can be classified into two general types:

(A) Fibrous webs; and (B) Substrates having open cells or pores, such as foams.

A porous, flexible fibrous web is comprised of a plurality of associated or interengaged fibers or structural elements having interstices or interstitial spaces defined therebetween. Preferred fibrous webs can include woven or non-woven fabrics. Other substrates include, but are not limited to, a matrix having open cells or pores therein such as foams or synthetic leathers.

The term "fiber", as used herein, refers to a long, pliable, cohesive, natural or man-made (synthetic) threadlike object, such as a monofilament, staple, filament, or the like. A fiber usable in this invention preferably has a length at least 100 times its diameter or width. Fibers can be regarded as being in the form of units which can be formed by known techniques into yarns or the like. Fibers can be formed by known techniques into woven or non-woven webs (especially fabrics) including weaving, knitting, braiding, felting, twisting, matting, needling, pressing, and the like. Preferably, fibers, such as those used for spinning, as into a yarn, or the like, have a length of at least about 5 millimeters. Fibers such as those derived from cellulosics of the type produced in paper manufacture can be used in combination with longer fibers as above indicated, as those skilled in the art will readily appreciate.

The term "filament" as used herein refers to a fiber of indefinite length.

The term "yarn" as used herein refers to a continuous strand comprised of a multiplicity of fibers, filaments, or the like in a bundled form, such as may be suitable for knitting, weaving or otherwise used to form a fabric. Yarn can be made from a number of fibers that are twisted together (spun yarn) or a number of filaments that are laid together without twist (a zero-twist yarn).

A flexible porous web used as a starting material in the present invention is generally and typically, essentially planar or flat and has generally opposed, parallel facing surfaces. Such a web is a three-dimensional structure comprised of a plurality of fibers with interstices therebetween or a matrix having open cells or pores therein. The matrix can be comprised of polymeric solids including fibrous and non-fibrous elements.

Non-fibrous elements, such as particulate fillers, binders, dyes, sizes and the like can be added to fibers in a web. Preferred webs have at least about 85% of their structure comprised of fibrous or fiber materials and are untreated with any sizing agent, coating, or the like.

Two principal classes of substrates having open pores or cells may be utilized in the present invention: leathers (including natural leathers, and man-made or synthetic leathers), and foamed plastic sheets (or films) having open cells.

Foamed plastic sheet or film substrates are produced either by compounding a foaming agent additive with resin or by injecting air or a volatile fluid into the still liquid polymer while it is being processed into a sheet or film. A foamed substrate has an internal structure characterized by a network of gas spaces, or cells, that make such foamed substrate less dense than the solid polymer. The foamed sheets or film substrates used as starting materials in the practice of this invention are flexible, open-celled structures.

Natural leathers suitable for use in this invention are typically split hides. Synthetic leathers have wide variations in composition (or structure) and properties, but they look like leather in the goods in which they are used. For purposes of technological description, synthetic leathers can be divided into two general categories: coated fabrics and poromerics.

Synthetic leathers which are poromerics are manufactured so as to resemble leather closely in breathability and moisture vapor permeability, as well as in workability, machinability, and other properties. The barrier and permeability properties normally are obtained by manufacturing a controlled microporous (open celled) structure.

Synthetic leathers which are coated fabrics, like poromerics, have a balance of physical properties and economic considerations. Usually the coating is either vinyl or urethane. Vinyl coatings can be either solid or expanded vinyl which has internal air bubbles which are usually a closed-cell type of foam. Because such structures usually have a non-porous exterior or front surface or face, such structures display poor breathability and moisture vapor transmission. However, since the interior or back surface or face is porous, such a coated fabric can be used in the practice of this invention by applying the polymer to the back face.

The fibers utilized in a porous flexible web treated by the methods and apparatus of the present invention can be of natural or synthetic origin. Mixtures of natural fibers and synthetic fibers can also be used. Examples of natural fibers include cotton, wool, silk, jute, linen, and the like. Examples of synthetic fibers include rayon, acetate, polyesters (including polyethyleneterephthalate), polyamides (including nylon), acrylics, olefins, aramids, azlons, glasses, modacrylics, novoloids, nytrils, rayons, sarans, spandex, vinal, vinyon, regenerated cellulose, cellulose acetates, and the like. Blends of natural and synthetic fibers can also be used.

With respect to the fluorocheinical liquid dispersions (or solutions) which can optionally be used for web pretreatment, the term "impregnation" refers to the penetration of such dispersions into a porous web, and to the distribution of such dispersions in a preferably, substantially uniform and controlled manner in such web, particularly as regards the surface portions of the individual web component structural elements and fibers.

With respect to the polymer compositions used in this invention, the term "controlled placement" or "placement" refers to the penetration of such polymer compositions into a porous web, to the distribution of such composition in a controlled manner through such web, and to the resultant, at least partial envelopment of at least a portion of the fibers of such web by such composition in accordance with the present invention, or to the formation of an internal layer, or both.

The word "thixotropy" refers herein to liquid flow behavior in which the viscosity of a liquid is reduced by shear agitation or stirring so as to allow the placement of the liquid flow to form: (a) a thin film of polymer composition encapsulating the structural elements making up the web leaving at least some of the interstitial spaces open; (b) an internal layer of a polymer composition between the upper and lower surfaces of the web; or (c) some combination of the foregoing. It is theorized to be caused by the breakdown of some loosely knit structure in the starting liquid that is built up during a period of rest (storage) and that is torn down during a period of suitable applied stress.

The term "coating" as used herein, refers to the application of a semi-liquid material to one or both sides of a textile material. Once the coating has been dried (and cured, if necessary), it forms a bond with the textile material.

The term "internal coating or internal layer" as used herein, refers to a region spaced from the outer surfaces of the web which is substantially continuously filled by the combination of the polymer controllably placed therein and the fibers and filaments of the web in the specified region. Such coating or layer envelopes, and/or surrounds, and/or encapsulates individual fibers, or lines cell or pore walls of the porous web or substrate, in the specified region. The internal layer is not necessarily flat but may undulate or meander through the web, occasionally even touching one or both surfaces of the web. Generally, the internal layer is exposed on both sides of a web as part of the multi complex structure of a woven and non-woven web. The thickness of the internal layer is generally in the range of 0.01 to 50 microns, and preferably in the range of about 0.1 to 20 microns.

The term "envelop" or "encapsulate" as used interchangeably herein, refers to the partial or complete surrounding, encasement, or enclosing by a discrete layer, film, coating, or the like, of exposed surface portions of at least some individual fiber or lining of a cell or pore wall of a porous web. Such a layer can sometimes be contiguous or integral with other portions of the same enveloping material which becomes deposited on internal areas of a web which are adjacent to such enveloping layer, enveloped fiber, lined cell or pore wall, or the like.

The term "elastomeric" as used herein refers to the ability of a cured polymer treated web to stretch and return to its original state.

The term "curing", or "cure", as used herein, refers to a change in state, condition, and/or structure in a material, such as a curable polymer composition that is usually, but not necessarily, induced by at least one applied variable, such as time, temperature, radiation, presence and quantity in such material of a curing catalyst or curing accelerator, or the like. The term "curing" or "cured" covers partial as well as complete curing. In the occurrence of curing in any case, such as the curing of such a polymer composition that has been selectively placed into a porous flexible substrate or web, the components of such a composition may experience occurrence of one or more of complete or partial (a) polymerization, (b) cross-linking, or (c) other reaction, depending upon the nature of the composition being cured, application variables, and presumably other factors. It is to be understood that the present invention includes polymers that are not cured after application or are only partially cured after application.

The term "filled" as used herein in relation to interstices, or interstitial spaces, or open cells, and to the amount of polymer composition therein in a given web, substrate, or the fibers in such web or substrate, designates the presence of such composition therein. When a given interstitial space or open cell is totally taken up by such composition, it is "completely filled" or "plugged". The term "filled" also refers to an interstitial space having a film or layer of polymer composition over or through it so that it is closed even though the entire thickness of the interstitial space is not completely filled or plugged.

Measurements of the degree of envelopment, interstitial fillage, plugging, or the like in an internal coating are conveniently made by microscopy, or preferably by conventional scanning electron microscopy (SEM) techniques. Because of the nature of such measuring by SEM for purposes of the present invention, "a completely filled" interstitial space or open cell can be regarded as a "plugged" interstitial space or open cell.

The term "on-line" as used herein means being controlled directly by or in direct communication with a computer.

The term "polymer", or "polymeric" as used herein, refers to monomers and oligomers as well as polymers and polymeric compositions, and mixtures thereof, to the extent that such compositions and mixtures are curable and shear thinnable.

The term "shear thinning", in its broadest sense, means the lowering of the viscosity of a material by the application of energy thereto.

A porous web or fabric is preferably untreated or scoured before being treated in accordance with the present invention. Preferably a web can be preliminarily treated, preferably saturated, for example, by padding, to substantially uniformly impregnate the web with a fluorochemical. Typically, and preferably, the treating composition comprises a dispersion of fluorochemical in a liquid carrier. The liquid carrier is preferably aqueous and can be driven off with heat after application. The treating composition has a low viscosity, typically comparable to the viscosity of water or less. After such a treatment, it is presently preferred that the resulting treated web exhibits a contact angle with water measured on an outer surface of the treated web that is greater than about 90 degrees. The treated web preferably contains fluorochemical substantially uniformly distributed therethrough. Thus, the fluorochemical is believed to be located primarily on and in the individual fibers, cells or pores with the web interstices or open cells being substantially free of fluorochemical.

A presently preferred concentration of fluorochemical in a treatment composition is typically in the range of about 1 to about 10% fluorochemical by weight of the total treating composition weight, and more preferably is about 2.5% of an aqueous treating dispersion. Web weight add-ons of the fluorochemical can vary depending upon such factors as the particular web treated, the polymer composition to be utilized in the next step of the treatment process of this invention, the ultimate intended use and properties of the treated web of this invention, and the like. The fluorochemical weight add-on is typically in the range of about 0.01 to about 5% of the weight of the untreated web. After fluorochemical controlled placement, the web is preferably squeezed to remove excess fluorochemical composition after which the web is heated or otherwise dried to evaporate carrier liquid and thereby also accomplish fluorochemical insolubilization or sintering, if permitted or possible with the particular composition used.

The fluorochemical treated web thereafter has a predetermined amount of a curable polymer composition controllably placed within the web by the methods and apparatus of this invention, to form a web whose fibers, cells or pores are at least partially enveloped or lined with the curable polymer composition, whose web outer surfaces are substantially free of the curable polymer, whose web interstices or open cells are not completely filled with the curable polymer and which may also contain an internal layer of polymer. The curable polymer composition utilized preferably exhibits a viscosity greater than 1,000 centipoise and less than 2,000,000 centipoise at rest at 25° C. at a shear rate of 10 reciprocal seconds.

The fluorochemical residue that remains after web treatment may not be exactly evenly distributed throughout the web, but may be present in the web in certain discontinuities. For example, these discontinuities may be randomly distributed in small areas upon an individual fiber's surface. However, the quantity and distribution of fluorochemical through a web is believed to be largely controllable. Some portions of the fluorochemical may become dislodged from the web and migrate through the polymer due to the forces incurred by the shear thinning and controlled placement of the polymer.

Fluorochemicals are sometimes known in the art as durable water repellent (DWR) chemicals, although such materials are typically believed to be not particularly durable and to have a tendency to wash out from a fabric treated therewith. In contrast, fiber enveloped webs of this invention which have been pretreated with a fluorochemical display excellent durability and washability characteristics. Indeed, the combination of fluorochemical pretreatment and silicone polymer fiber envelopment such as provided by the present invention appears to provide synergistic property enhancement because the effects or properties obtained appear to be better than can be obtained than by using either the fluorochemical or the silicone polymer alone for web treatment.

In a preferred procedure of fluorochemical controlled placement, a web is substantially completely saturated with an aqueous dispersion of a fluorochemical. Thereafter, the resulting impregnated web is compressed to remove excess portions of said dispersion. Finally, the web is heated to evaporate the carrier liquid. If the fluorochemical is curable, then the heating also accomplishes curing. After the fluorochemical treatment, the fluorochemical is found only on or in the web structural elements or fibers and is substantially completely absent from the web interstices.

The fluorochemical concentration in the treating composition is such as to permit a treated fluorochemical containing web, after volatiles of the treating composition are removed, to exhibit a contact angle with water applied to an outer web surface which is greater than about 90°. More preferably, the contact angle provided is greater than about 130°.

The web weight add-on provided by the fluorochemical after removal of volatiles is usually relatively minor. However, the weight add on can vary with such factors as the nature of web treated, the type of polymer composition utilized in the next step of the process, the temperature at which the composition is applied, the ultimate use contemplated for a web, and the like.

The fluorochemical particularly, and also the bonding agents when used, are preferably affixed to the three-dimensional structure of the web prior to the controlled placement of polymer within the web. Complete affixing is not necessary for the fluorochemical. The fluorochemical will apparently facilitate the pressured application of a polymer composition even if the fluorochemical is not preliminarily fixed within or located within the web being treated. However, fixing, especially by sintering, appears to cause the water repellent chemicals to flow and to become better attached to the three-dimensional structure of the web. In this regard, a lesser amount of fluorochemical will remain in place better, and will better facilitate the subsequent pressured application of the polymer, if the sintering or insolubilizing step is performed prior to such a pressured application.

The curable polymer composition is believed to be typically polymeric, (usually a mixture of co-curable polymers and oligomers), and to include a catalyst to promote the cure. The polymers that can be used in the present invention may be monomers or partially polymerized polymers commonly known as oligomers, or completely polymerized polymers. The polymer may be curable, partially curable or not curable depending upon the desired physical characteristics of the final product. The polymer composition can include conventional additives.

While silicone is a preferred composition, other polymer compositions can include, polyurethanes, fluorosilicones, silicone-modified polyurethanes, acrylics, polytetrafluoroethylene-containing materials, and the like, either alone or in combination with silicones.

It is to be understood that the depth of polymer placement into a web can be controlled by the methods and apparatus herein described to provide selective placement of the polymer within the substrate or web. The web is thereafter optionally cured to convert the curable composition into a solid elastomeric polymer.

The polymer composition is theorized to be caused to flow and distribute itself over fibers, cells or pores in a web under the influence of the processing conditions and apparatus provided by this invention. This flow and distribution is further theorized to be facilitated and promoted by the presence of a fluorochemical which has been preliminarily impregnated into a web, as taught herein. The amount of fluorochemical or fluorochemical residue in a web is believed to influence the amount, and the locations, where the polymer will collect and deposit, and produce encapsulated fibers and/or an internal layer in the web. However, there is no intent to be bound herein by theory.

Some portion of the residue of fluorochemical resulting, from a preliminary web saturating operation is theorized to be present upon a treated fiber's surfaces after envelopment of fibers, cells or pores by the polymer has been achieved during the formation of the encapsulating fiber and/or the internal layer by the practice of this invention. This is believed to be demonstrated by the fact that a web treated by this invention still exhibits an enhanced water and oil repellency, such as is typical of fluorochemicals in porous webs. It is therefore believed that the fluorochemicals are affecting the adherence of the polymer as a thin film enveloping layer about the treated fibers, cells or pores as well as facilitating polymer pressurized flow within and about the interstices or open cells of the web being treated so that the polymer can assume its position enveloping the fibers or lining the cells or pores of the substrate.

In those fabrics that are pretreated with fluorochemicals, the exact interrelationship between the polymer film and the impregnated fluorochemical is presently difficult, or perhaps impossible, to quantify because of the variables involved and because transparent polymer is difficult to observe by optical microscopy. It can be theorized that perhaps the polymer and the fluorochemical each tend to produce discontinuous films upon the fiber surface, and that such films are discontinuous in a complementary manner. It may alternatively be theorized that perhaps the polymer film is contiguous, or substantially so, relative to fluorochemical molecules on a fiber surface, and that the layer of polymer on a fiber surface is so thin that any dislodgement of the fluorochemical may release the fluorochemical into the polymer film thereby allowing the fluorine to orient or project through the film with the required cure temperature of the polymer, reactivating the water surface contact angle so that the water repellent properties of the fluorochemical affect the finished product. However, regardless of physical or chemical explanation, the combination of polymer film and fluorochemical results in a fiber envelopment or cell or pore wall lining and the formation of encapsulated fibers and/or an internal layer of polymer in a web when this invention is practiced. After curing, the polymer is permanently fixed material.

By using the methods and apparatus of this invention, one can achieve a controlled placement of a polymer composition into a porous substrate or web to obtain a desired treated web.

A curable polymer such as used in the practice of this invention is applied under pressure using shear forces onto and into a web or substrate. The shear forces cause the curable silicone polymer to flow in to the web. The extent of fiber envelopment and cell or pore wall lining is believed to be regulatable by controlling such factors as discussed previously, as well as the selection and applied amount of fluorochemical, if any, the curable polymer used, and the applied compressive and shear forces employed at a given temperature so that fiber envelopment is achieved while the interstices and/or open cells of the web are not completely filled with such polymer in the region of the internal layer, and the outer opposed surfaces of the web are substantially completely free of polymer coating or residue. After such a procedure, the curable polymer is then cured.

The curable polymer is applied onto the surface of the web. Then, the web, while tensioned, is passed over and against shearing means or through a compression zone, such as between rollers or against a shear knife. Thus, transversely applied shear force and compressive pressure is applied to the web. The combination of tension, shearing forces, and web speed is sufficient to cause the polymer to move into the web and out from the interstices or open cells around the web fibers, cells, or pores being enveloped. The result is that at least some of the interstices and/or open cells are unfilled in regions of the web outside of the region occupied by the internal coating or internal layer, and are preferably substantially free of polymer. Excess polymer is removed by the surface wiping action of the shearing means. The curable polymer enveloping the fibers is thereafter cured.

The desired penetration of, and distribution and placement of polymer in, a web is believed to be achieved by localized pressuring forces exerted on a web surface which are sufficiently high to cause the viscosity of a polymer composition to be locally reduced, thereby permitting such polymer to flow under such pressuring and to be controllably placed within the web and to envelope its fibers or line the cell or pore walls thereof. To aid in this process, the web is preferably at least slightly distorted by tensioning or stretching, while being somewhat transversely compressed at the location of the controlled placement. This distortion is believed to facilitate the entrance of the polymer composition into the web. When the compression and tension are released, the polymer composition is believed to be squeezed or compressed within and through the interstitial spaces, or open cell spaces, of the treated web.

If, for example, too much polymer is present in the finished product, then either or both the tension and shear force can be increased, and vice versa for too little polymer. If flow is not adequate upon the fibers, producing incomplete fiber envelopment, then the viscosity of the polymer composition can be reduced by increasing the pressures and temperatures employed for the controlled placement thereof. Alternatively, if the viscosity is too low, then the pressure and/or temperature can be decreased. If the polymer composition is resistant to being positioned or placed in a desired location in a desired amount in a given web at various viscosities and/or pressures, then the level of fluorochemical pretreatment of the web can be increased, or decreased, as the case may be.

As indicated above, the activity transpiring at a final step in the practice of this invention is generically referred to as curing. Conventional curing conditions known in the prior art for curing polymer compositions are generally suitable for use in the practice of this invention. Thus, temperatures in the range of about 250° F. to about 350° F. are used and times in the range of about 30 seconds to about 1 minute can be used, although longer and shorter curing times and temperatures may be used, if desired, when thermal curing is practiced. Radiation curing, as with an electron beam or ultraviolet light can also be used. However, using platinum catalysts to accelerate the cure while using lower temperatures and shorter cure times is preferable.

Since either filled, plugged, almost filled interstices, or open cells in the region of an internal layer remain transmissive of air in cured webs made by this invention, the webs are characteristically air permeable or breathable.

Sample webs or fabrics that are beneficially treated, fiber enveloped and internally coated in accordance with the invention include nylon, cotton, rayon and acrylic fabrics, as well as fabrics that are blends of fiber types. Sample nylon fabrics include lime ice, hot coral, raspberry pulp, and diva blue Tactel® (registered trademark of ICI Americas, Inc.) fabrics available from agent Arthur Kahn, Inc. Sample cotton fabrics include Intrepid® cotton cornsilk, sagebrush cotton, and light blue cotton fabrics available also from Arthur Kahn, Inc. Non-woven, monofilamentous, fabrics such as TYVEK® (registered trademark of E. I. duPont de Nemours Co., Inc.) and the like are also employable.

A curable polymer composition utilized in the practice of this invention preferably has a viscosity that is sufficient to achieve an internal coating of the web. Generally, the viscosity is greater than about 1000 centipoise and less than about 2,000,000 centipoise at a shear rate of 10 reciprocal seconds. It is presently most preferred that such composition have a viscosity in the range of about 5,000 to about 1,000,000 centipoise at 25° C. Such a composition is believed to contain less than about 1% by weight of volatile material.

The polymer is believed to be typically polymeric and to be commonly a mixture of co-curable polymers, oligomers, and/or monomers. A catalyst is usually also present, and, for the presently preferred silicone polymer compositions discussed hereinafter, is platinum or a platinum compound, such as a platinum salt.

A preferred class of liquid curable silicone polymer compositions comprises a curable mixture of the following components:

(A) at least one organo-hydiosilane polymer (including copolymers);

(B) at least one vinyl substituted polysiloxane (including copolymers);

(C) a platinum or platinum containing catalyst; and (D) (optionally) fillers and additives.

Typical silicone hydrides (component A) are polymethylhydrosiloxanes which are dimethyl siloxane copolymers. Typical vinyl terminated siloxanes are vinyidimethyl terminated or vinyl substituted polydimethylsiloxanes. Typical catalyst systems include solutions or complexes of chloroplatinic acid in alcohols, ethers, divinylsiloxanes, and cyclic vinyl siloxanes.

The polymethylhydrosiloxanes (component A) are used in the form of their dimethyl copolymers because their reactivity is more controllable than that of the homopolymers and because they result in tougher polymers with a lower cross-link density. Although the reaction with vinyl functional silicones (component B) does reportedly take place in 1:1 stoichiometry, the minimum ratio of hydride (component A) to vinyl (component B) in commercial products is reportedly about 2:1 and may be as high as 6:1. While the hydroxylation reaction of polymethylhydrosilane is used in both so called RTV (room temperature vulcanizable) and LTV (low temperature vulcanizable) systems, and while both such systems are believed to be useful in the practice of the present invention, systems which undergo curing at elevated temperature are presently preferred.

Elastomers produced from such a curing reaction are known to demonstrate toughness, tensile strength, and dimensional stability.

Particulate fillers are known to be useful additives for incorporation into liquid silicone polymer compositions. Such fillers apparently not only can extend and reinforce the cured compositions produced therefrom, but also can favorably influence thixotropic behavior in such compositions. Thixotropic behavior is presently preferred in compositions used in the practice of this invention. A terminal silanol (Si—OH) group makes such silanol siloxanes susceptible to reaction in curing, as is believed desirable.

It is believed that all or a part of component B can be replaced with a so called silanol vinyl terminated polysiloxane while using an organotin compound as a suitable curing catalyst as is disclosed in U.S. Pat. No. 4,162,356. However, it is presently preferred to use vinyl substituted polysiloxanes in component B.

A polymer composition useful in this invention can contain curable silicone resin, curable polyurethane, curable fluorosilicone, curable modified polyurethane silicones, curable modified silicone polyurethanes, curable acrylics, polytetrafluoroethylene, and the like, either alone or in combination with one or more compositions.

One particular type of silicone composition which is believed to be well suited for use in the controlled placement step of the method of the invention is taught in U.S. Pat. Nos. 4,472,470 and 4,500,584 and in U.S. Pat. Nos. 4,666,765; 5,004,643; and 5,209,965. The contents of these patents are incorporated herein by reference. Silicone resin compositions shown in the table below have all been used in the practice of this invention. Such compositions of Table I are believed to involve formulations that are of the type hereinabove characterized.

TABLE I

Illustrative Starting Polymer Compositions

| MANUFACTURER | TRADE DESIGNATION | COMPONENTS[1] |
|---|---|---|
| Mobay | Silopren ® LSR 2530 | Vinyl-terminated polydimethylsiloxane with fumed silica, methylhydrogen siloxane |
| Mobay | Silopren ® LSR 2540/01 | |
| Dow Corning | Silastic ® 595 LSR | Polysiloxane |
| General Electric | SLE 5100 | Polysiloxane |
| General Electric | SLE 5106 | Siloxane resin solution |
| General Electric | SLE 5300 | Polysiloxane |
| General Electric | SLE 5500 | Polysiloxane |
| Shin-Etsu | KE 1917 | |
| Shin-Etsu | DI 1940-30 | |
| SWS Silicones Corporation | Liquid Rubber BC-10 | Silicone fluid with silicone dioxide filler and curing agents |
| GE SLE 5110 | | Polysiloxane |
| GE SLE 6108 | | Polysiloxane |

Table I footnote:
[1]Identified components do not represent complete composition of the individual products shown.

In such compositions useful in the present invention, a control of compositional rheology, and particularly of complex viscosity, is accomplishable, if desired, by the selective addition of diluent and additives. These polymer compositions characteristically exhibit performance curves indicating substantially level and constant loss modulus, storage modulus, and complex viscosity over extended temperature ranges. The graphic plots of loss modulus, storage modulus, and complex viscosity versus temperature all are believed to characteristically exhibit a sharp knee that shows the moduli to increase in value rapidly at cure temperatures.

Preferably, the curing proceeds to a point where the polymer composition is no longer sticky, or tacky, but preferably curing is not allowed to continue to a point where the resulting polymer composition becomes excessively hard, rigid, or brittle. Compositions of this invention are controllably curable into polymeric materials which are preferably not sticky or tacky, and which have desirable elastomeric, flexural, and resiliency characteristics.

The polymer composition used in the practice of this invention can also carry additives into the three-dimensional structure of the web during the pressured application. Further, it is preferable, that any additives be bound into the cured composition permanently as located in the three-dimensional structure of the web. Particularly in the case of fabrics, this desirably positions the additives mainly on surface portions of the encapsulated yarns and fibers in positions where they typically are beneficially located and maintained, or on the surfaces of the internal layer, or on the surfaces of the web, or some combination thereof.

Control of the pressurized application step can be provided at a number of areas since the shear process is sensitive to the viscosity of the polymer composition both at atmospheric pressure and at superatmospheric pressure. The ambient temperature affecting the polymer as it is applied, and the pressure-induced temperature changes occurring during controlled placement of the polymer also play roles in viscosity and therefore the shear process. Of course, the chemical composition of the polymer composition also plays a role in the shear process and assists in the formation of an internal layer and/or internal encapsulation of the fibers or structural elements of the web.

The amount of polymer utilized and the weight add-on thereof are again variable and dependent upon several things such as the treated web, the desired end use of the web, cost and the like. Web weight add-ons can be as little as about 5 weight percent up to about 200 weight percent of the untreated web. For producing breathable, water-repellent fabric webs of this invention, weight add-ons are preferably in the range of about 10 to about 100 weight percent of the weight of the untreated web.

The pressured application of the polymer is sensitive to the viscosity of the polymer composition. Temperature affects the polymer composition by reducing or altering its viscosity. Shear-induced temperature changes occurring during application or during subsequent shear processing of the polymer can affect viscosity. The chemical composition of the polymer also plays a role in the treating process and effects in the treatment of web structural elements (including fibers) and the regulation of the filling of interstices and open cell voids.

Various machines and procedures can be used for performing the process of the invention. Illustrative machines and processes of use which are suitable for use in the practice of this invention, are now described.

FIG. 1 depicts a schematic, side elevational view of one embodiment or methods and apparatus for practicing the present invention. In this embodiment a continuous web 302 is moved under tension along a web pathway from a supply roll 301 to a take-up roll 327.

The primary tension is a result of the differential rate between the driven entrance pull stand designated as 306 and the driven exit pull stand designated as 322, whereby the exit pull stand 322 is driven at a rate faster than the entrance pull stand 306. Other controllable factors which effect tension are the diameters of blade rolls 309, 314, 316, 318; the vertical depth of blades 311, 315, 317; the durometer of the entrance pull stand rolls 304, 305 and rubber roll 321 of the exit pull stand, and the friction as the web passes under the blades.

Web 302 passes between the nip of the two rolls 304 and 305 of the entry pull stand 306. The entry nip is adjustable to produce a force of from about 100 lbs. to about 5 tons on the web, passing between the two rolls. The weight of top roll 305 provides an even distribution of force throughout the web width. Web 302 is flattened at this point and the interstitial spaces are reduced laterally and longitudinally. Bottom roll 304 has micro-positioning capability to provide for gap adjustment and alignment. The top roll 305 composition is chosen based on the durometer of a urethane or rubber roll.

Figure 8:
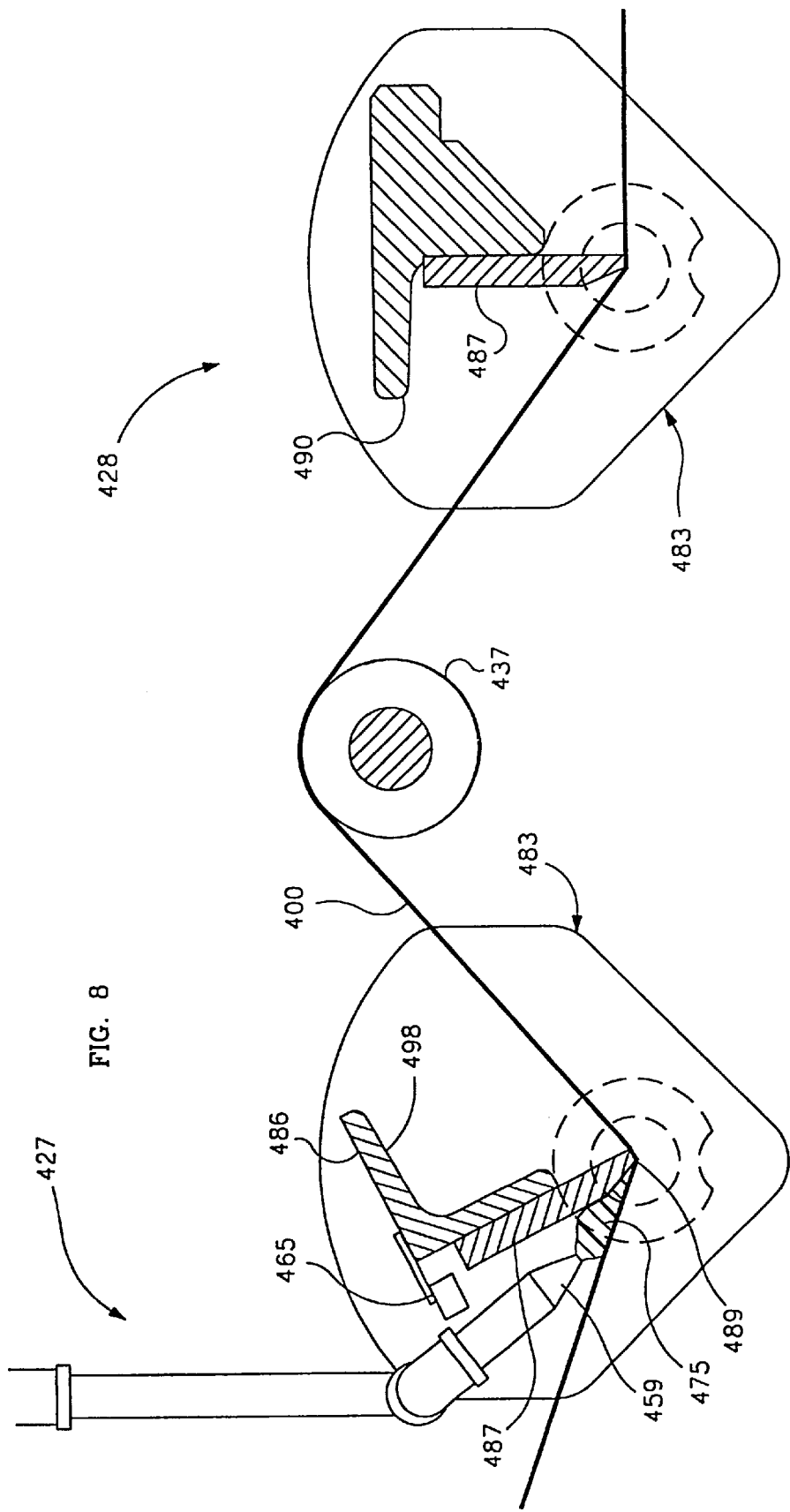
FIG. 8 is an enlarged partially cross-sectioned view depicting the knife blades at the first and second process heads and also illustrating the polymer dispensing apparatus.

Web 302 continues to move along past idler roll 308 and blade roll 309 and forms an entry angle $\alpha$ and an exit angle $\beta$ with blade 311. For purposes of the apparatus of FIG. 1, the blade has a leading edge and a trailing edge as shown in FIG. 8. Entry angle $\alpha$ can be varied by adjusting: (a) the height and diameter of blade rolls 309 and 314, (b) the horizontal position of blade rolls 309 and 314, (c) the angle of blade 311, and (d) the height of blade 311. Similarly, the entry and exit angles of blades 315 and 317, can be varied by adjusting the same devices surrounding each blade.

For illustrative purposes, increasing the height and diameter of blade roll 309 decreases entry angle $\alpha$. Rotating blade 311 clockwise, with web 302 running left to right, increases entry angle $\alpha$. Likewise, rotating blade 311 counterclockwise, with web 302 running left to right, decreases entry angle $\alpha$. Decreasing the distance between blade roll 309 and blade 311 decreases entry angle $\alpha$. Increasing the downward depth of blade 311 into web 302 decreases entry angle $\alpha$.

The angle of blades 311, 315, and 317 are completely changeable and fully rotational to 360°. The fully rotational axis provides an opportunity for more than one blade per rotational axis. Therefore, a second blade having a different thickness, bevel, shape, resonance, texture, or material can be mounted. Ideally the apparatus contains two or three blades per blade mount. The blade mounts are not shown.

The force or pressure of blade 311 applied against web 302 is determined by the vertical positioning of blade 311 in the blade mount. The greater the downward depth of blade 311, the greater the force or pressure. Blade pressure against the web is also accomplished through the tension of the web as described above.

The same line components that affect entry angle $\alpha$, also affect exit angle $\beta$. Any changes in the height, diameter, or horizontal positioning of blade rolls 309 and 314, affects exit angle $\beta$. If the angle of blade 311 is rotated clockwise as described above, entry angle $\alpha$ increases, thus decreasing exit angle $\beta$.

As web 302 moves from left to right in FIG. 1, polymer is deposited on web 302 with polymer applicator or dispersion means 310. Polymer applicator 310 can be a pump, a hose, or any available application device for applying polymer onto the surface of the web. Polymer applicator 310 is located directly in front of blade 311. The polymer is immediately shear thinned, placed into, and extracted from web 302 by the leading edge of blade 311, thus controlling the amount of polymer remaining in web 302. The bevel of blade 311 can effect entry angle $\alpha$ and the sharpness of the leading edge of blade 311. A sharper leading edge has a greater ability to push the weave or structural elements of web 302 longitudinally and traversely, increasing the size of the interstitial spaces. As the web passes the leading edge of blade 311, the interstitial spaces snap back or contract to their original size.

As web 302 moves from left to right in FIG. 1, the process of shear thinning and placing polymer into and extracting it out of web 302 is repeated at subsequent blades 315 and 317, thus controllably placing the polymer throughout web 302. Web 302 then passes over idler roll 319 and between driven exit pull stand 322 which consists of rolls 320 and 321. Pull roll 320 is a driven roll proportionally driven at a predetermined rate slower than entry roll 304. Pull roll 321 does not apply pressure so much as it achieves a high degree of surface area in which web 302 must come into contact with. The larger the surface area, the higher the degree of contact friction. Pull roll 321 can be adjusted to have sufficient downward force to eliminate any slippage between web 302 and pull roll 320.

After web 302 passes from exit stand 322, it then moves into an oven 323 for curing. Rolls 324, 325, and 326 provide a tension regulating means and also serve to provide a cooling pathway for web 302 as it emerges from oven 323 before passing onto take-up roll 327.

The cure temperature of oven 323 is thermostatically controlled to a predetermined temperature for web 302 and the polymers used. Machine runs of new webs are first tested with hand pulls to determine adhesion, cure temperature, potentials of performance values, drapability, aesthetics, etc. The effect on web 302 depends on the temperature of oven 323, dwell time and curing rate of the polymer. Web 302 may expand slightly from the heat.

Oven 323 functions to cure the polymer composition that is controllably placed into web 302. Oven 323 can be operated with gas or other energy sources. Furthermore, oven 323 could utilize radiant heat, induction heat, convection, microwave energy or other suitable means for effecting a cure. Oven 323 can extend from about 12 to 20 yards, with 15 yards long being convenient.

Curing temperatures from about 320° F. to about 500° F., applied for times of from about two minutes to about thirty seconds (depending on the temperature and the polymer composition) are desirable. If a curing accelerator is present in the polymer, curing temperatures can be dropped down to temperatures of about 265° F. or even lower (with times remaining in the range indicated).

The cure temperature of oven 323 and the source and type of cure energy, are controlled for a number of reasons. The cure temperature of oven 323 is controlled to achieve the desired crosslinked state; either partial or full. The source and type of energy can also affect the placement of the polymer and additives. In place of an oven, or in combination with an oven, a source of radiation can be employed (electron beams, ultraviolet light, or the like) to accomplish curing, if desired. For example, by using a high degree of specific infrared and some convection heat energy for cure, some additives can be staged to migrate and/or bloom to the polymer surfaces.

Oven cure dwell time is the duration of time the web is in oven 323. Oven cure dwell time is determined by the speed of the oven's conveyor and physical length of the oven. If the dwell time and temperature for a particular web is at maximum, then the oven conveyor speed would dictate the speed of the entire process line or the length of the oven would have to be extended in order to increase the dwell time to assure proper final curing of the web.

Take-up roll 327 is operated at approximately the same speed as supply roll 301. When the rotational speeds of take-up roll 327 are not synchronized with rotational speeds of supply roll 301, the tension roll combination of rolls 324, 325, and 326 can be used to reduce web slack.

Web speed is proportional to the variable speed of the motor which drives entrance pull stand 306 and exit pull stand 322. Web speed can effect the physics of the polymers as web 302 passes under blades 311, 315, and 317. Web transport speeds can vary widely; for example, from about two yards per minute to about ninety yards per minute.

Figure 2:
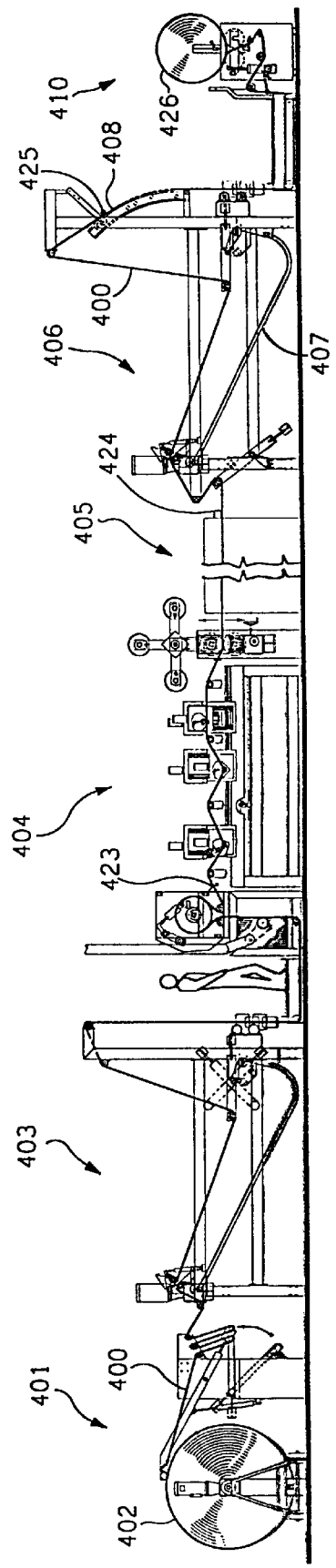
FIG. 2 is an overall view of the presently preferred apparatus for use in the practice of the present invention.

Referring to FIG. 2, there is shown a schematic side elevational view of a preferred method and apparatus for practicing the subject invention. In this method and apparatus a continuous web 400 is moved along a web pathway from a supply roll zone generally designated as 401 to a take-up or rewind roll zone generally designated as 410. The line includes the supply roll zone 401 which includes a supply roll 402, an entry scray drive zone generally designated as 403, the processing zone generally designated as 404, the curing zone generally designated as 405, an exit scray drive zone generally designated as 406, and the rewind roll zone 410. The supply roll zone 401 and rewind roll zone 410 are conventional in nature. The entry scray zone 403 is used to generally straighten out the web and reduce wrinkles. It also straightens and guides the web into the processing zone. This equipment is also conventional and well known in the art. The web passes under a static bar 423 before entering the processing zone 404 which is discussed more fully hereinafter. The curing zone 405 contains a plurality of ovens, or one oven with a plurality of heating zones, for curing the treated web 400. Preferably, the first oven applies infrared energy to the treated side of the web. Additional convection and/or radiant heat is applied at a temperature and time to partially or completely cure the treated web as desired. During the cure the web is supported in a suitable fashion so that no transverse or longitudinal tension is applied to the web so that the web remains in the same state as it is in just after the processing zone. The relaxed state of the web is obtained by transporting the web along a belt, a bed of air, or the like. By allowing the web to remain in a relaxed state, there is no adverse affect to (a) the thin film encapsulation of the individual fibers and filaments, (b) the controlled placement of the internal coating, and (c) the controlled placement of additives in (a) and (b). Preferably, a non-conductive, heat resistant, open mesh belt, made out of Kevlar® is used to transport the web through the curing zone. Other heat resistant materials could be used to transport the web through the curing zone. The cured web passes under another static bar 424 as it exits the curing zone. The exit scray zone 406 includes facilities 407 for allowing the treated web 400 to accumulate if it is not rewound on rewind roll 426 fast enough. Also, the exit scray zone 406 has a lighted inspection panel 408 where an operator can view the passing web to determine the physical quality of the treated web. A static bar 425 is positioned above the inspection panel 408 to remove static from the web before it is wound on rewind roll 426.

Figure 3:
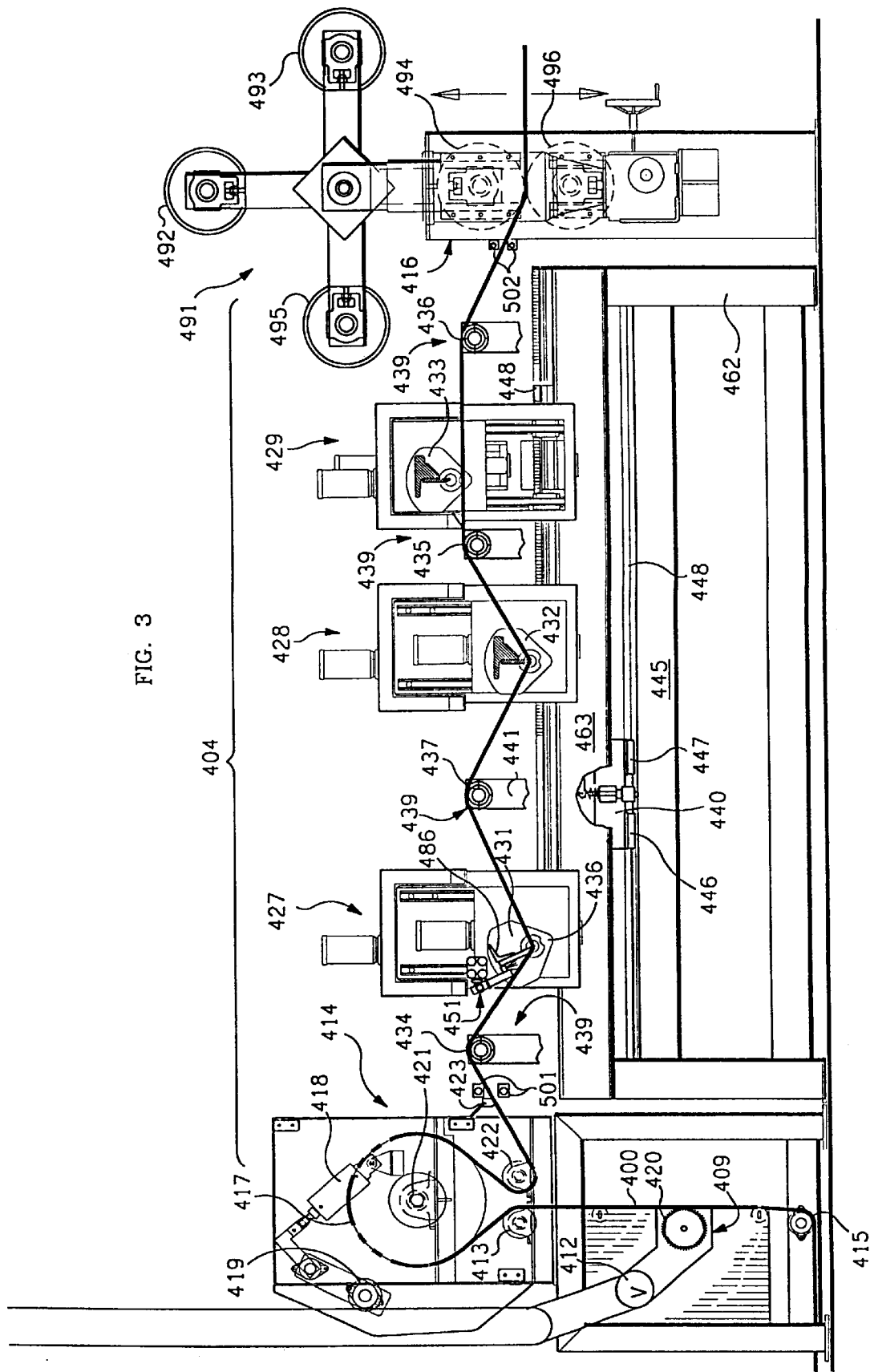
FIG. 3 is an enlarged partially cross-sectioned view of the processing zone of the apparatus shown in FIG. 2.

Referring to FIG. 3 for additional detail of the processing zone 404, the web 400 is shown passing over an idler roll 415 and past a vacuum device generally designated as 409 which removes lint from the web 400. The vacuum device 409 includes a rotatable lint brush 420 which brushes against the web, and a suction tube 412 which removes lint and dust particles from the surface of the web 400 to be treated. The web 400 then passes upwardly over a guide roll 413 and over the brake roll 417 of the brake stand generally designated as 414. The brake stand 414 operates independently or in conjunction with the pull stand generally designated as 416 as the primary tension control of the web in the processing zone 404. In use, the brake stand 414 could be neutral while the pull stand 416 pulls the web 400 through the processing station. Alternatively, the brake stand 414 could run in reverse or at a speed equal to or slower than the pull stand to apply tension to the web 400. The independent control of the brake stand 414 and pull stand 416 allows a greater degree of tension control and a wider range of tension than conventional master-slave arrangements of the pull and brake stands.

The brake stand 414 includes the brake roll 417 which has a changeable roll cover thereon which is selected to minimize slippage of the web relative to the brake roll 417. A hydraulic cylinder 418 is selectively actuated to move a nip roll 419 into engagement with the web 400. The pneumatic rubber nip roll 419 preferably is applied lightly to the web 400 to avoid crushing the web. This nip roll 419 is usually used only if the web 400 slips about the brake roll 417. The web 400 leaves the brake roll 417 past a tension roll 422 which measures the tension of the web 400 at this point. Tension can also be measured at roll 413, if desired. The tension rolls referred to herein contain transducers which convert web tension into a D.C. voltage which is proportional to tension. Tension rolls of this type are manufactured by Dover Flexo Electronics, Inc. of Rochester, N.H. This type of tension roll measures tension across the entire length of the roll and provides an output proportional to the average of the tension. Other ways of measuring tension include adding load cells to the ends of a roll. The brake stand 414 configuration shown herein avoids crushing the web 400 prior to treatment as opposed to passing the web through a pair of hard nip rolls. If crushing is not an issue, a nip stand could be used in place of the brake stand. The brake stand 414 is controlled by computer control of a motor (not shown) which drives a shaft 421 connected to brake roll 417. The web 400 leaves the brake stand 414 and passes under a static bar designated as 423. The static bar 423 removes substantially all static electricity from the surface of the web to be treated prior to the web entering the processing zone 404. This is necessary to prevent arcing from the web 400 to any metal parts which the web is in proximity to. It has also been found desirable to remove static electricity by static bars 424 and 425 after the web 400 exits the curing zone 405 and prior to the inspection light panel 408 as shown in FIG. 2. Static bars may also be positioned at other places, if desired.

The processing zone 404 consists of a plurality of process heads 427, 428 and 429. While three process heads are shown, in any given application one, two or three may be utilized. In addition, additional process heads could be added to the processing zone 404, if desired. Each process head is moveable horizontally in the processing zone as described more fully hereinafter. Also, each process head has a blade holding assembly generally designated as 431, 432 and 433, described more fully hereinafter, which moves each blade vertically up and down and also rotates the blade to the desired angle relative to the moving web 400.

In addition to the process heads 427, 428 and 429, the processing zone 404 has a plurality of adjustable idler roll assemblies generally designated as 439 for further controlling the tension in the web 400. While only one idler roll assembly 439 is shown in detail between process heads 427 and 428, similar idler roll assemblies have mounted thereto idler roll 434 shown positioned in front of the first process head 427, idler roll 435 positioned between process heads 428 and 429, and idler roll 436 positioned after process head 429 and before the pull stand 416. All of these idler roll assemblies are adjustable horizontally as described below in reference to FIG. 4. They can also be adjustable vertically, by the use of spacers or other facilities known in the art.

Figure 4:
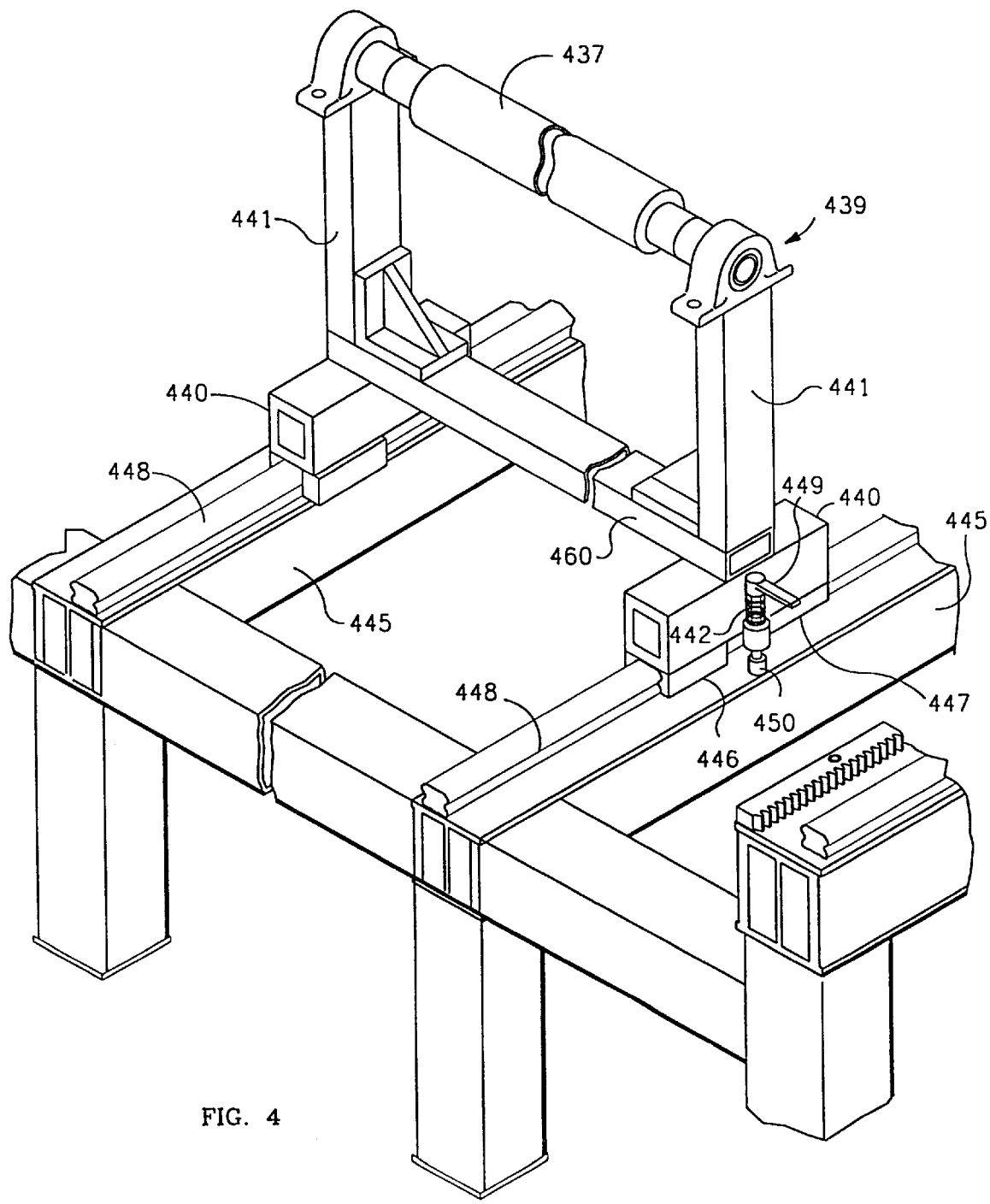
FIG. 4 is a perspective view of the idler roll assemblies shown in FIG. 3.

Referring to FIG. 4, there is shown a representative idler roll assembly 439. Each side of the assembly includes a base member 440 which has a vertical support 441 on which is mounted a rotatable idler roll such as 437. The base member 440 of the idler roll assembly 439 has mounted to the bottom thereof a plurality of carriages 446 and 447 which are movable on a rail 448 which runs along the entire side frame 445 of the processing zone apparatus. Each base member 440 has a locking mechanism mounted thereto which includes a latch 449 which has a rubber bushing 450 on the bottom end which is biased downwardly by a spring 442. The latch 449 can be pivoted downwardly against spring 442 to force the bushing 450 against the base member 440 to lock the base member 440 to the frame 445 when the desired horizontal position is reached. A similar base 440 and vertical support 441 is mounted on the other side of the machine and is interconnected by a support 460 so that both base members 440 can be moved along their respective rails 448 in parallel.

Figure 5:
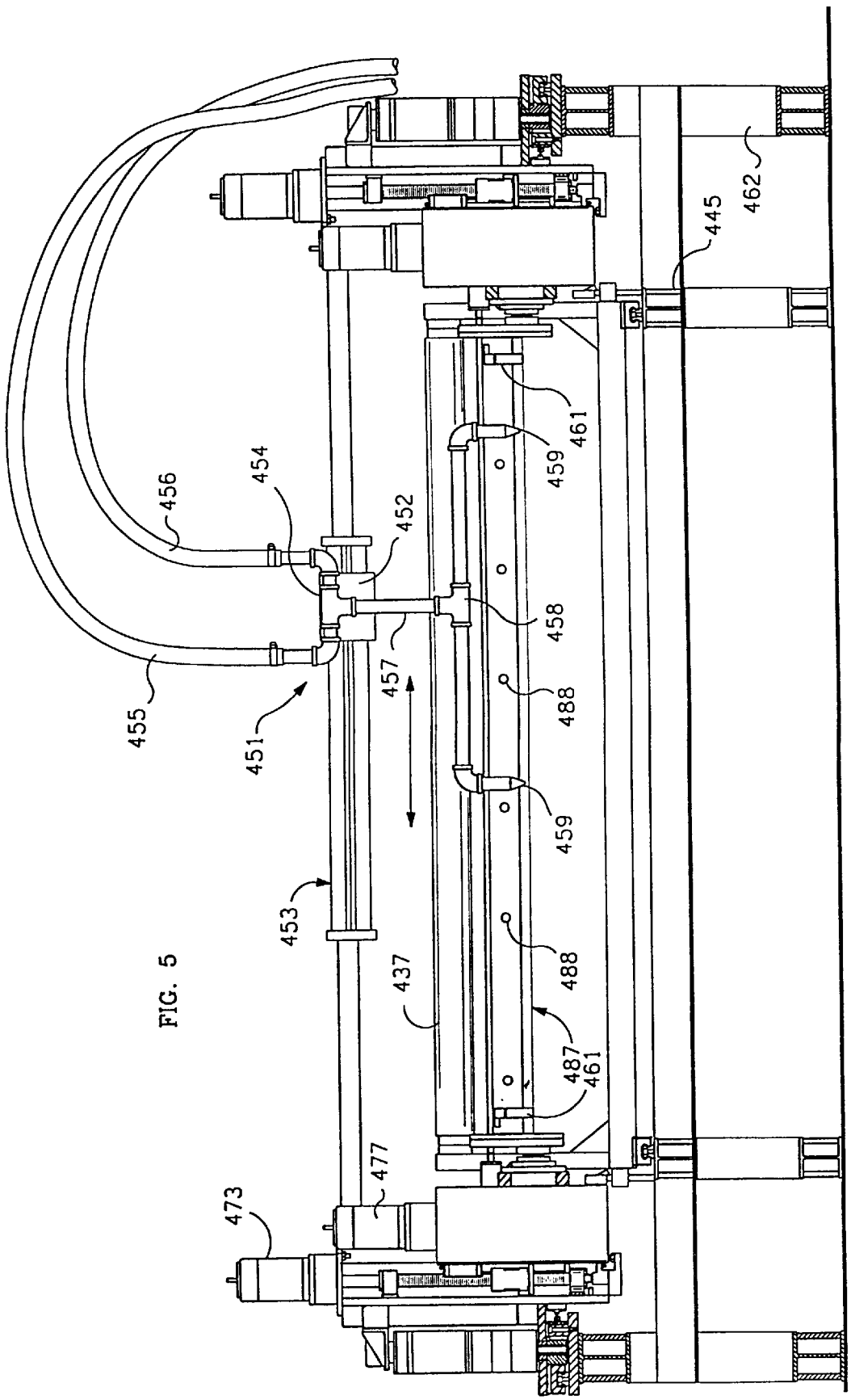
FIG. 5 is a view of the polymer dispensing apparatus on the first process head.

Referring to FIGS. 3 and 5, there is shown a polymer applicator or dispensing unit generally designated as 451 which is mounted to the front of the first process head 427. The polymer applicator unit 451 includes a plate 452 which is reciprocated transversely across the web by a conventional reciprocating tube 453 such as a Tol-O-Matic, Inc. model BC 215 band cylinder. The plate 452 has a tee 454 mounted thereto. The materials to be applied to the web 400 are introduced to the tee 454 in any desired ratio. A first polymer is introduced under pressure via tube 455 from a storage tank (not shown) positioned remotely from the machine. A second polymer, additive or other material is introduced under pressure into tube 456 from another remote storage tank. The materials are mixed together within a static mixer 457 and are dispensed through another tee 458 into a spaced pair of nozzles 459 onto the moving web 400. The static mixer 457 includes a rotatable screw thread or corkscrew therein (not shown) which rotates due to flow of the materials therethrough and causes mixing of the materials. The static mixer is conventional and can be of the type distributed by Environmental Spray Systems, Incorporated. Alternatively, other static or dynamic mixers well known in the art, may be used to obtain more pre-shearing and mixing of the polymers. The amount of material dispensed is controlled by controlling the flow rate through tubes 455 and 456 in a pre-determined ratio so that a suitable amount of material is applied to the web 400 directly in front of the blade. The nozzles 459 are positioned to dispense the mixed material or polymer composition directly in front of the blade 487 as shown in FIGS. 5 and 8. Dams 461 are mounted at each end of the blade 487 to prevent the polymer bead 475 from flowing off the edge of the web 400. An ultrasonic sensor 465 is positioned on the blade support member 486 for measuring the size of the polymer bead 475 applied in front of the blade 487 by the nozzles 459. The ultrasonic sensor 465 provides a signal to the computer 503 described hereinafter which in turn controls the flow of the polymers or other materials through the tubes 455 and 456 to increase or decrease the flow as desired. Other sensors may be utilized to monitor the size of the polymer bead 475. If the polymer bead became too large, it can have a negative affect on the ability of the blade to shear thin the polymer. In some instances too large a bead may cause globs of polymer to be forced under the blade edge without adequate shear thinning. A polymer applicator 451 with connections for dispensing more than two materials may also be utilized where it is desired to mix in multiple polymers, or a polymer with multiple additives. Alternatively, instead of depositing the polymer directly on the web, it may be deposited on a sloped plate or trough (not shown) positioned in front of the blade 487 to limit the exposure of the web to the polymer in a prescribed area directly in front of the blade. While the polymer applicator 451 is shown attached to the first process head 427, it may be positioned on process head 428 or 429 if the preceding process heads are not being used. Alternatively, it may be desired to use a polymer applicator 451 on more than one process head.

Referring now to FIGS. 6 and 7, there are shown the facilities for moving the process heads 427, 428 and 429 horizontally. The three process heads are mounted on a frame assembly 462 as shown in FIG. 3. The frame assembly 462 includes a plurality of vertical and horizontal support members, including a pair of parallel horizontal side supports 463, only one of which is shown. One side support 463 is mounted on opposite sides of the machine spaced from the transverse ends of the web 400. Mounted to the side support 463 and running along its length is a rail 464 and a rack 448. Each process head 427, 428 and 429 includes a carriage generally designated as 466, which rides on the rail 464. The carriage 466 has connected thereto a pair of carriage blocks 467 and 468 which fit over the rail 464 as shown in FIGS. 6 and 7. The carriage 466 has mounted thereto a stepper motor 469 which rotates a shaft 471 to turn a pinion gear 472. The pinion gear 472 engages the rack 448 and when energized moves the carriage 466 to the precise desired position horizontally along the rail 464 and rack 448.

The facilities for moving the blade holding assembly 431 vertically and angularly is also shown in FIG. 6. The arrangement for blade holding assemblies 432 and 433 is the same. The vertical movement of a housing 450 connected to the blade holding assembly 431 is controlled by a stepper motor 473 which turns a screw thread 474. Rotation of the screw thread 474 engages a threaded block 460 connected to the housing 450 to cause housing 450 to move vertically, guided by carriage blocks 455 which move along a pair of guide rails (not shown) mounted on either side of screw thread 474. The carriage blocks 455 and associated guide rails are similar in structure to the carriage blocks 467 and 468 moving along rail 464 as described in connection with the horizontal movement of carriage 466. The rotation of the blade holding assembly 431 to set the angle of the blade 487 relative to the web 400 is controlled by a stepper motor 477 which rotates a shaft 478 to turn a worm gear 479. The rotation of the worm gear 479 turns gear 481 which in turn rotates the shaft 482 which rotates the blade end support assembly 483. The blade end support assembly 483 includes a portion 485 thereof connected to the shaft 482 for rotational movement therewith.

Affixed to the blade end support assembly 483 is an end support plate 484 to which is mounted an L-shaped blade support member 486 as shown in FIG. 8 which traverses the width of the machine. The support 486 is a large steel support of substantial mass to reduce vibrations in the blade and prevent any flexing thereof. One end of the blade support member 486 is fastened to the end support plate 484 on one side of the machine, and the other end is attached to a similar end support plate (not shown) on the other side of the machine. The L-shaped blade support member 486 for process head 427 has its top flange 498 facing rearward (in the direction of travel of the web) in order allow the operator to view the polymer bead 475 applied in front of the blade 487. On process heads 428 and 429 a more massive blade support member 490 is used to provide maximum support for the blade 487 and to minimize vibration. Each blade 487 is mounted to its respective blade support member 486 or 490 at multiple places along its length. The blade 487 has plurality of load cells 488 (see FIG. 5) spaced uniformly along its length for measuring tension. Load cells 488 are mounted in holes within each blade 487 and measure the force of the web 400 against the blade. This force is converted into tension to measure the tension of the web at the leading edge 489 of the blade. The blade is mounted to the blade support member 486 or 490 so that the leading edge 489 of the blade 487 is axially aligned with the axis of rotation of the blade end support assembly 483 as shown in FIG. 8. This allows precise control of the entry angle and exit angle of the web relative to the blade. Consequently, a one degree rotation of the blade changes the entry angle and exit angle by one degree. If desired, the blade holding assemblies 431, 432 and 433 could hold a plurality of different blades, each of which could be selectively rotated into engagement with the web 400. This arrangement would have the axis of rotation at the center of the end support plate 484 as opposed to the preferred axis of rotation which is aligned with the leading edge 489 of the blade 487. Each of the stepper motors 469, 473 and 477 on each process head can be accurately controlled to obtain precise horizontal, vertical and angular positioning. The stepper motors are typically computer controlled, but may be controlled manually, if desired.

Referring again to FIG. 3, it is preferred to use a pull stand 416 that has independently driven rolls 494 and 496 which may be driven in the same or different directions to provide better control of tension of the web. Alternatively, the pull stand 416 may have a turret generally designated as 491 holding a plurality of rolls 492, 493, 494 and 495 of different durometer. The turret can be rotated so that a roll of the desired durometer is used to engage the driven roll 496 of the pull stand 416 to pull the web 400 through the process zone 404. In using a roll of softer durometer, a greater image area or footprint is obtained on the web 400, lowering the force per unit area applied to the web and thus lowering the secondary shearing force. By using a harder durometer, a smaller footprint is obtained, increasing the force per unit area applied to the web and thus increasing the secondary shearing force. Alternatively, you can obtain a greater image area by using more pressure between the rolls. Both roll hardness and pressure are selectively adjusted as desired.

Quality Control Loop

Figure 9:
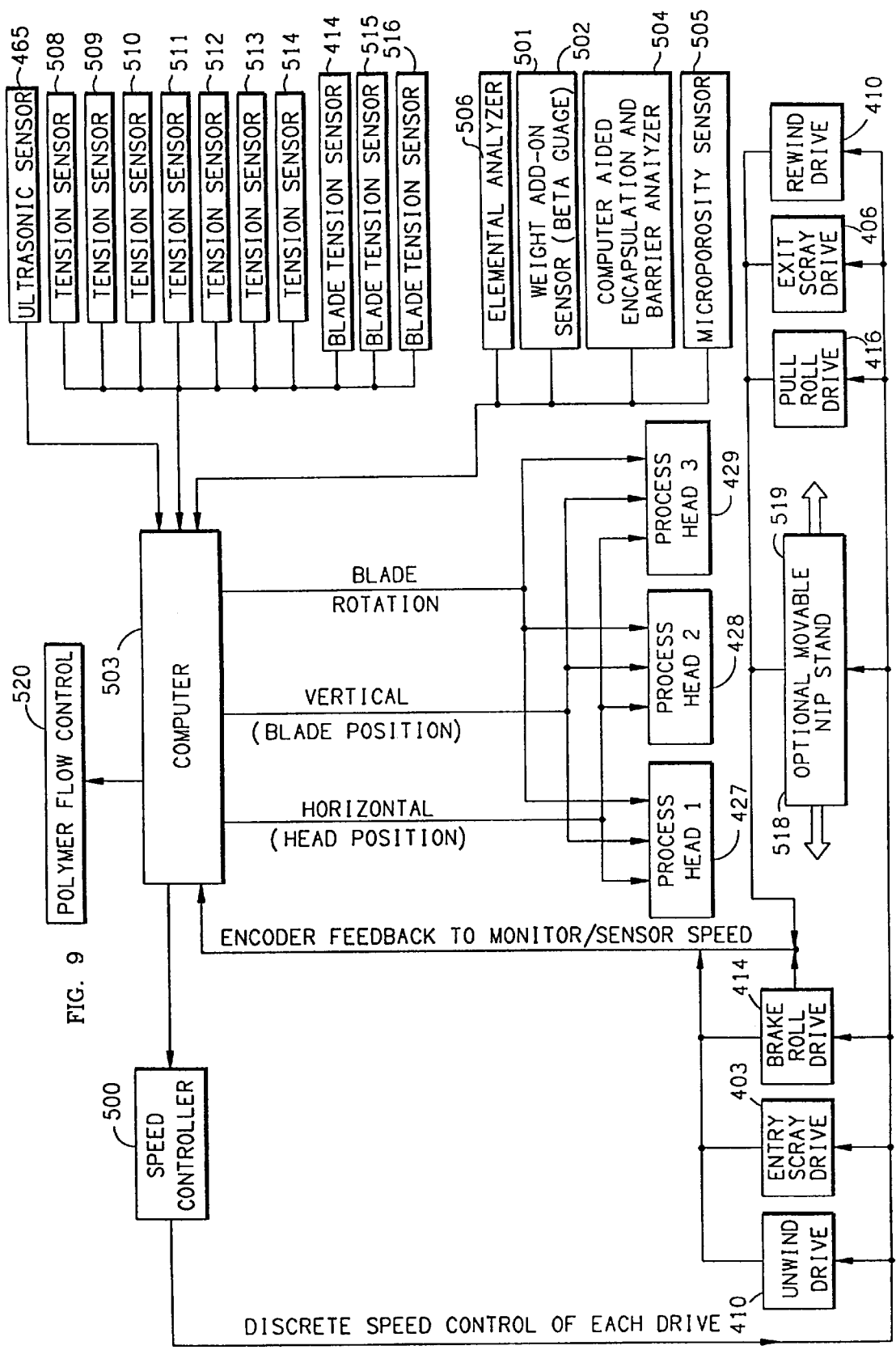
FIG. 9 is a block diagram illustrating the control of various parameters in accordance with the subject method and apparatus.

Referring to FIG. 9, there is shown a block diagram of the quality control loop of the process and apparatus of the subject invention. There are a plurality of parameters to be determined in order to have appropriate quality control of the process and apparatus. One parameter is to determine the weight add on of the polymer by use of a pair of beta gage sensors 501 and 502. Each sensor includes a transmitter and a receiver placed above and below the web respectively. The beta gage sensors are positioned as shown in FIG. 3 to measure the density of the web 400 before treatment, and to measure the density of the web 400 after treatment. To determine the polymer weight add on percentage, the web density is measured before the polymer is added, and then is measured after the polymer is added. The change in density is attributed to the polymer composition added to the web and is converted to a weight percentage add on. A predetermined desired weight add on percentage is inputted into the computer 503 for comparison purposes. If high weight add on is measured, it could mean there is a thick coating on the web which could be caused by low tension, high polymer viscosity, and/or low shear forces. The potential solutions are to increase tension, increase shear forces on the polymer and/or start with a lower viscosity polymer. A high weight add on may also mean that there is saturation of the web. This may be caused by too much polymer, low polymer viscosity, high shear force, and/or insufficient extraction of the polymer. The solution is to decrease polymer flow, decrease shear forces on the polymer, start with a higher viscosity polymer, increase the angle of the blade or blades, and/or increase tension. A high weight add on measurement might also mean that there is an encapsulated web with an internal layer formed therein which is too thick. This may be caused by low tension, high polymer viscosity, low shear forces, and/or insufficient extraction of polymer. The solution is to increase tension, increase shear forces on the polymer, start with a lower viscosity polymer, increase blade angle, and/or increase tension.

If an acceptable weight add on is measured, it may mean that there is an encapsulated web and/or an internal layer of appropriate thickness. If a very low weight add on is measured, it means there may be too thin or no coating, not much encapsulation or no saturation. The potential causes for this are not enough polymer, low tension, a pressure difference too small to measure, or the polymer viscosity is extremely low. The potential solution for this is to add more polymer, increase the tension or increase polymer viscosity.

Another parameter to be measured is the placement of the internal layer of polymer in the web. This is done with a computer aided encapsulation and barrier analyzer designated as 504, which is an image gathering device used after curing the web. During the application of the polymer to the web, a section along the edge of the web is treated with a polymer composition containing a marker such as, but not limited to, a fluorescent material or metal particles. After curing the treated web, the specially treated edge is slit by a slitting device. The slit in the web is necessary in order to allow a view of the cross-section of the specially treated edge. The slit edge then travels into an enclosed area where energy of some form is transmitted across the cross-section of the slit edge, creating an image of the marker material and creating a pattern. The energy can be in the form of, but not limited to, wavelengths of infrared, ultraviolet, x-ray, or ultrasonic pulses, as well as radioactive particles, and the like. The pattern developed will appear as a density distribution of particles that can be shown as images on a computer screen. The distribution can be compared with a set distribution input into the computer for comparison purposes, in order to determine the placement of the internal layer. Ideally, the computer will compare the distribution of the marker to the set point values. If the layer is not within the acceptable range then the density distribution will appear outside the set point established for that particular web. If the scattering is disbursed throughout the web, it may mean that there is a saturation in the web which can be caused by too much polymer, low polymer viscosity, high shear force, and/or insufficient extraction of the polymer. The potential solutions are to decrease polymer flow, decrease the shear forces on the polymer, start with a higher viscosity polymer, or start with a lower viscosity polymer. If the scattering determines that there is a layer that is not within the acceptable range, this may be caused by low tension, high polymer viscosity and/or low shear forces. In such a case, the solution is to increase tension, increase the shear forces on the polymer, or start with a lower viscosity polymer. If the analyzer determines that the internal layer is placed too close to the treated side of the web, it may mean there is insufficient polymer, and/or insufficient extraction of the polymer. The solution is to increase polymer flow, increase blade angle, and/or increase tension. If the analyzer determines that the internal layer is placed too close to the untreated side of the web, it may mean that there is too much polymer, and/or excessive extraction of the polymer. If the scattering determines the layer is in the acceptable range, this means that there is an internal layer of polymer that is properly positioned.

Another parameter to be measured is microporosity. A microporosity sensor 505 is used to measure the pressure drop through an area of the web 400. The web travels over an enclosed area where air is pressured through the web before treatment and then after cure, and the change or difference in pressure is measured. This pressure difference is converted into an effective porosity which is directly proportional to the amount of free space in or effective porosity of the web. The effective porosity of the treated and untreated web are compared to indicate the degree of breathability or microporosity. This sensor 505 alone cannot determine encapsulation of the fibers or structural elements of the web, but can be used in combination with the other measurement devices disclosed herein to indicate whether a web is encapsulated or not. If a large pressure difference is measured, it may mean there is an external coating of polymer on the web surface which is undesirable and which may be caused by low tension, high polymer viscosity, and/or low shear forces. The potential solution is to increase tension, increase the shear forces on the polymer, and/or start with a lower viscosity polymer. If there is a large pressure difference, it may also mean there is an internal layer that is too thick. This is caused when there is too much polymer, and/or insufficient extraction of polymer. In this case, polymer flow may be decreased, blade angle may be increased, and/or tension may be increased. A large pressure difference may also indicate a saturation condition caused by too much polymer, low polymer viscosity, high shear force, and/or insufficient extraction of the polymer. The solution is to decrease polymer flow, decrease the shear forces on the polymer, start with a higher viscosity polymer, increase the blade angle, and/or increase tension. If an untreated web lacks uniformity and shows large pressure drop variations, but once treated, the pressure drop levels off, it may mean that polymer is filling in the voids of the non-uniform web. If this is the desired result, nothing should be changed. If not, a more uniform untreated web should be used. If the pressure difference is small, it means there is an encapsulated web with an internal layer. If the pressure difference is zero, it may mean that there is little or no encapsulation, no internal layer, or no saturation. This can be caused by too little polymer, pressure differences that are too small to measure, or the polymer viscosity could be extremely low. The pressure difference range for acceptable products either is stored in the computer or is entered by an operator for each different product. The preset range is used for comparing against the measured values.

Another measurement device utilized herein is an elemental analyzer 506 using an energy source, such as, but not limited to, an x-ray. This device analyzes the elemental make-up at a localized section of a web by a method of x-ray florescence. The web travels through an enclosed area where the untreated side of the web is eradiated by the primary beam or a beam from a secondary target. The energy will travel through the web, creating a particular signature of the specific element being examined. Signatures of known elements are input to the computer for comparison purposes against what is measured. For example, a web having silicone on it will show a signature different than a web that has no silicone present. This device will indicate whether the polymer composition has flowed throughout the web. This device alone cannot determine encapsulation of fibers, but can be used in combination with the other devices above to indicate whether a web is encapsulated or not. If the analyzer 506 detects polymer on the untreated side of the web, it is indicative of encapsulation. It could also mean there is saturation of the web, which could be caused by too much polymer, low polymer viscosity, high shear force, and/or insufficient extraction of polymer. If so, the polymer flow could be decreased, the shear forces on the polymer could be decreased, a higher viscosity polymer could be used, the blade angle could be increased, and/or the tension could be increased. If the device indicates polymer on the untreated side of the web, it may mean the voids or interstices of the web are filled without there being encapsulation. This could be caused by insufficient polymer, excessive extraction of the polymer, low tension, high polymer viscosity, and/or low shear forces. The solution is to increase polymer flow, increase shear forces on the polymer, increase tension, and/or start with a lower viscosity polymer. If the analyzer 506 detects little or no polymer on the untreated side of the web, it could mean an internal layer is formed with encapsulation not extending to the untreated side of the web. If this is desired, nothing needs to be changed. If not, this may be caused by insufficient polymer, low tension, high polymer viscosity, and/or low shear forces. The solution is to increase polymer flow, increase shear forces on the polymer, increase tension, and/or start with a lower viscosity polymer. If there is no polymer detected, it could also mean there is a coating of polymer on the treated side of the web which may be caused by low tension, high polymer viscosity, and/or low shear forces. This can be corrected by increasing the tension in the web, increasing the shear forces on the polymer, or using a lower viscosity polymer. The foregoing devices 501 and 502, 504, 505 and 506 can be combined to give a more accurate picture of what is actually occurring with the polymer in the web. Based on such information, the computer can alter various variables on the machine, as discussed below.

Also inputted into the computer 503 are outputs from a plurality of tension sensors designated as 508, 509, 510, 511, 512, 513, 514, 515, 516 and 517. These tension sensors are either tension rolls of the transducer type previously described or load cells attached to the ends of the idler rolls which generate a signal proportional to the tension applied to the web at a specific roll.

Tension is controlled by a variety of devices in the subject apparatus and process. More specifically, tension is controlled by driven nip stands, the positioning of the blades, the positioning of the idler rolls and the polymer rheology and viscosity. It is apparent from the invention that a plurality of nip stands could be used at various places in the processing zone to create various macro-tension zones between the nip stands. Each nip stand can be independently operated to run forward, backward or neutral. Each nip stand can be a different size, weight and have different durometer rolls to leave different footprints and to control slippage. The speed and direction of each nip stand is controlled by a speed controller which is controlled by a computer monitoring the tension in each zone as described hereinafter. Each roll of each nip stand can be independently operated to cause a controlled differential roll speed. The viscosity and flow characteristics of the polymer effects the tension of the web. Each web would react differently with different types of polymers. The tension is effected in much the same way as a rope's tension is altered when wet. Tension will vary all along with the type of web and the type of polymer utilized.

Figure 10:
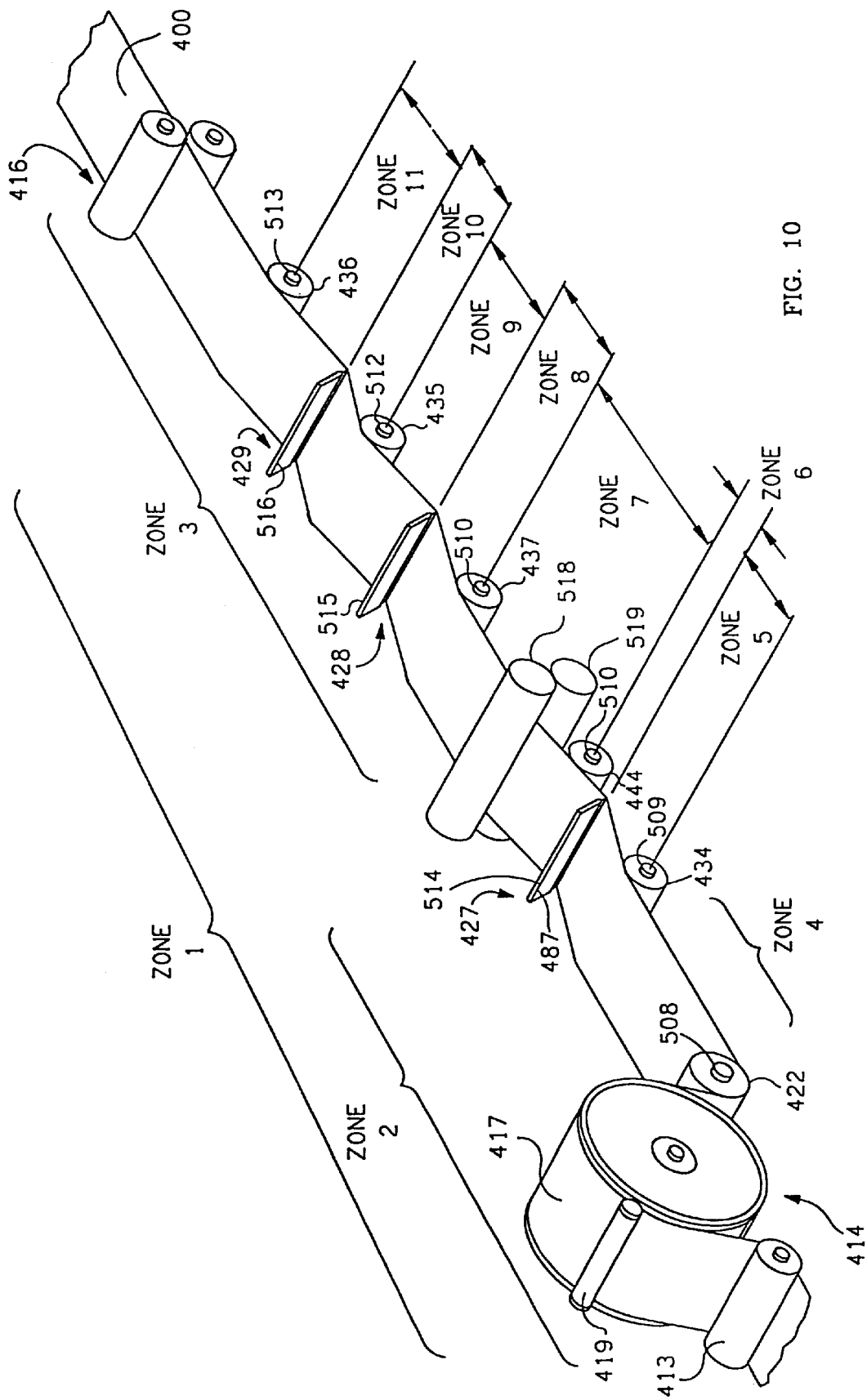
FIG. 10 is a perspective view diagrammatically illustrating the various zones of tension which may be established to control the apparatus and method in accordance with the present invention.

Referring to FIG. 10, the tension sensor 508 is measured by a load cell or transducer in the idler roll 422. The tension sensor 509 is measured by a load cell or transducer in an idler roll 434. The tension sensor 510 is measured by a load cell or transducer in idler roll 444. The tension sensor 511 is measured by a load cell or transducer in idler roll 437. The tension sensor 512 is measured by a load cell or transducer in idler roll 435. The tension sensor 513 is measured by the idler roll 436. The first blade tension sensor 514 is measured by load cells in the blade 487 in process head 427. The second blade tension sensor 515 is measured by load cells in the blade 487 in process head 428. The third tension sensor 516 is measured by load cells in the blade 487 in process head 429. The load cells across each blade 487 are averaged to give an average tension signal per blade. Each sensor 508–516 generates a signal to the computer which is proportional to the tension applied to the web at that point.

The three primary or macro-zones of tension are zones 1, 2 and 3. Macro zones are created between nip stands. The zone 1 tension is applied between the brake stand 414 and the pull stand 416. The zone 2 tension is applied between an optional pair of nip rolls 518 and 519 and the brake stand 414. The zone 3 tension is applied between nip rolls 518 and 519 and the pull stand 416. The secondary or micro-zones of tension are zones 4–11. Micro-zones are created between idler rolls or an idler roll and a blade. The zone 4 tension is applied between the roll 422 and the idler roll 434. The zone 5 tension is applied between the idler 434 and the blade 487 of process head 427. The zone 6 tension is applied between the blade 487 of process head 427 and an optional idler roll 444 positioned before the optional nip rolls 518 and 519. The zone 7 tension is applied between the idler roll 444 and the idler roll 437. The zone 8 tension is between idler roll 437 and the blade 487 of process head 428. The zone 9 tension is between the blade 487 of process head 428 and the idler roll 435. The zone 10 tension is between idler roll 435 and the blade of 487 of process head 429. The zone 11 tension is between the blade 487 of process head 429 and the idler roll 436.

Different zones of tension are selectively established to get better encapsulation and/or better control of the internal layer in the web 400. Breaking the web into macro zones of tension allows for a lowering of the overall tension in any one particular zone. For example, if the nip rolls 518 and 519 are not used, the tension at each place in zone 1 increases from the brake stand 414 to the pull stand 416. With the introduction of nip rolls 518 and 519, zone 1 is divided into two macro zones, namely zone 2 and zone 3. Zone 3 can now have a lower tension than zone 2, if desired. It may also have an equal or higher tension, if desired. Similarly, other nip rolls could be placed in the processing zone 404 to create further macro zones of tension. With micro tension zones, a better degree of control over the tension at any blade is attained. The overall tension within any tension zone can be measured in a variety of ways, including but not limited to, selecting one tension sensor as representative of tension within the specific tension zone, or averaging several sensors within the selected tension zone to provide a representative tension.

Referring again to FIG. 9, the computer 503 receives outputs from the tension sensors 508–516, the weight add-on sensors 501 and 502, the computer aided encapsulation and barrier analyzer 504, the microporosity sensor 505 and the elemental analyzer 506. From this data, the computer provides an output to one or more speed controllers 500 for controlling each of the unwind roll drive 401, entry scray drive 403 and brake roll drive 414. The computer 503 also provides an output to speed controller 500 to control the pull stand drive 416, the exit scray drive 406 and the rewind drive 410. Further, the speed controller 500 also controls the drives (not shown) for optional nip rolls 518 and 519. All of the computer controlled drives provide a feedback signal to the computer to allow constant monitoring. The computer 503 also receives a signal from the ultrasonic sensor 465 to control a polymer flow rate control 520. The computer also outputs information for controlling the blade rotation or blade angle, the vertical height of the carriage and the horizontal position of each process head 427, 428 and 429.

The computer is capable of comparing various sensed inputs against preset ranges of parameters for a particular product, described herein and controlling various machine elements to produce an on-line process control. The computer analysis and control allows for multiple variable controlled manufacturing and product development that was previously unachievable with single variable, manual control, primarily because of the level of multiple variable statistical comparisons that the compute can achieve.

A presently preferred web which is both fluorochemical and silicone polymer treated and which is breathable, water resistant and rewashable is characterized as being a longitudinally tensionable porous flexible fibrous web having opposed substantially parallel surfaces that are comprised of associated fibers with interstices between the fibers, or is a matrix having cells or pores therein. The web is substantially uniformly impregnated with a fluorochemical and thereafter treated with a silicone polymer composition, to form a web having an internal layer within the web wherein the outer surfaces of the web are substantially free of silicone polymer and the web is breathable and water resistant or waterproof. At least a portion of the fibers or cell walls are encapsulated or enveloped. At least one surface of the web is characterized by having a visual appearance which is substantially the same as the visual appearance of one surface of the starting porous web.

When the web has fibers comprised of a synthetic polymer, the polymer is preferably selected from the group consisting of polyamides, polyesters, polyolefins, regenerated cellulose, cellulose acetate, and mixtures thereof.

Preferred webs of this invention are more specifically characterized by having a water drop contact angle in the range of about 90° to about 160°; a rewash capability of at least about 3; a breathability of at least about 35% of untreated substrate web; and a water repellency rating of at least about 80 prior to washing.

A general process for making a porous web of this invention comprises the steps of: tensioning a flexible, porous web as above characterized, applying a curable shear thinnable polymer composition to at least one web surface and then moving over and against one surface of the tensioned web a uniformly applied localized shear force to: shear thin the polymer composition, uniformly place the composition within the web, at least partially individually encapsulate or envelop surface portions of at least some of said fibers through the web matrix or position said composition in a desired web internal region or some combination of both. Thereafter, the web is subjected to conditions sufficient to cure the composition in said web. Curing is accomplished by heat, by radiation, or both.

Typically, webs of this invention are characterized by having fiber envelopment layers which range from about 0.01 to about 50 microns.

A presently preferred process for making a fluorochemical and silicone resin treated web having breathability, water resistance and rewashability which is adapted for continuous operation comprises the successive steps of: impregnating the web with a fluorochemical, longitudinally tensioning the fluorochemical impregnated web while sequentially first applying to one surface thereof a curable silicone polymer composition and concurrently applying a transversely exerted localized compressive force against said surface, and moving over said surface of the web substantially rigid shearing means which exerts transversely an applied, localized shear force against said surface to shear thin the polymer and wipe away exposed portions of silicone polymer composition on said surface, thereby forming an internal layer of silicone polymer and/or enveloping at least some of the fibers or passageways through the matrix, or both; and curing the silicone polymer composition in the web.

Theory

The following text concerns the theory of the invention as it is now understood; however, there is no intent herein to be bound by such theory.

The presently preferred polymer composition used in the treatment of webs by this invention is a non-Newtonian liquid exhibiting thixotropic, pseudoplastic behavior. Such a liquid is temporarily lowered in viscosity by high pressure shear forces.

One aspect of the invention is a recognition that when high forces or sufficient energy are applied to curable polymer compositions, the viscosities of these materials can be greatly reduced. Conversely, when subjected to curing, the same liquid composition sets to a solid form which can have a consistency comparable to that of a hard elastomeric rubber. The internal and external rheological control of polymer materials achieved by the present invention is believed to be of an extreme level, even for thixotropes. When subjected to shear force, the polymer composition is shear thinned and can flow more readily, perhaps comparably, to water.

The invention preferably employs a combination of: (i) mechanical pressure to shear thin and place a polymer composition into a porous web; (ii) an optional porous web pretreatment with a water repellent chemical, such as a fluorochemical, which is theorized to reduce the surface tension characteristics of the web and create a favorable surface contact angle between the polymer composition and the treated web which subsequently allows, under pressure and shear force exerted upon an applied polymer composition, the production and creation of an internal coating or layer which envelopes fibers or lines cell walls in a localized region within the web as a result of polymer flow in the web or which encapsulates the fibers within the web; and (iii) a polymer composition impregnant preferably having favorable rheological and viscosity properties which responds to such working pressures and forces, and is controllably placed into, and distributed in a web. This combination produces a web having the capability for a high degree of performance. This product is achieved through pressure controlled placement and applied shear forces brought to bear upon a web so as to cause controlled movement and flow of a polymer composition into and through a web. Preferably, repeated compressive applications of pressure or successive applications of localized shear forces upon the polymer in the web are employed.

Thixotropic behavior is preferably built into a polymer used in the invention by either polymer selection or design or additive/filler design. For example, it now appears that thixotropic behavior can be accentuated by introducing into a polymer composition certain additives that are believed to impart enhanced thixotropy to the resulting composition. A lower viscosity at high shear rates (during application to a web) is believed to facilitate polymer flow and application to a web, whereas a polymer with high viscosity, or applied at a low shear rate (before and/or after application) actually may retard or prevent structural element (including fiber) envelopment or encapsulation.

Although the present invention has now been described in terms of certain preferred embodiments and exemplified with respect thereto, one skilled in the art will readily appreciate the various modifications, changes, omissions, and substitutions that may be made without departing from the spirit and scope of the invention as set forth in the following claims.

What is claimed is:

1. Apparatus for controlling placement of a polymer composition into a moving porous web having a plurality of structural elements with interstitial spaces therebetween comprising:

means for applying tension to the porous web within a processing zone;

means for applying a shear-thinnable polymer composition onto a surface of a tensioned web;

means for shear thinning the polymer composition to substantially reduce its viscosity and selectively place it into the tensioned web leaving at least some of the interstitial spaces open, said shear thinning means including at least one process head having a rigid knife blade mounted thereto transversely to said moving web for engagement of said moving web;

means for selectively positioning said process head within said processing zone;

means mounted to said process head for selectively positioning said knife blade vertically and rotationally against said moving web; and means for curing a treated web.

2. Apparatus as set forth in claim 1 further comprising means for supporting the web during cure so that there is substantially no transverse or longitudinal tension on the web.

3. Apparatus as set forth in claim 1 wherein the knife blade has a leading edge in contact with said moving web and the axis of rotation of said knife blade is coincident with said leading edge.

4. Apparatus as set forth in claim 1 wherein said polymer applying means comprises:

at least one nozzle;

means for reciprocating the nozzle transversely across the moving web;

a supply for each material in the polymer composition;

means for mixing the materials of said polymer composition;

means connecting said supply to said mixing means and said mixing means to said nozzle; and means for pumping material from each supply at a desired ratio to said mixer means.

5. Apparatus as set forth in claim 4 wherein said mixing means is mounted to said reciprocating means for movement with said nozzle.

6. Apparatus as set forth in claim 1 including means for measuring an amount of the polymer composition applied to the moving web.

7. Apparatus as set forth in claim 6 including means responsive to said measuring means for controlling a flow rate of said pumping means.

8. Apparatus as set forth in claim 1 including at least two process heads and further including a nip stand positioned intermediate said process heads for lowering the tension in the moving web between the nip stand and the end of the processing zone.

9. Apparatus as set forth in claim 8 wherein said tension applying means includes:

a first idler roll positioned between a first process head and said nip stand;

a second idler roll positioned between said nip stand and a second process head; and a third idler roll positioned after said second process head.

10. Apparatus as set forth in claim 9 wherein said idler rolls are adjustable horizontally and vertically.

11. Apparatus as set forth in claim 1 wherein said polymer applying means includes means for controlling a flow rate of a plurality of materials used in the polymer composition and for mixing said materials in a desired ratio.

12. Apparatus as set forth in claim 11 wherein said polymer applying means includes means for reducing viscosity of the polymer composition prior to application to the web.

13. Apparatus as set forth in claim 1 including:

means for monitoring an amount of polymer composition applied to the moving web; and means responsive to said monitoring means for controlling said polymer applying means.

14. Apparatus as set forth in claim 1 including:

means for measuring the tension of the web within said processing zone; and means responsive to tension measurement for controlling said knife blade positioning means.

15. Apparatus as set forth in claim 1 wherein said means for measuring tension comprises means for measuring force of said moving web against said knife blade and for generating a signal representative of average tension of the web across said knife blade.

16. Apparatus as set forth in claim 1 wherein said shear thinning means includes at least two process heads mounted within said processing zone, said second process head spaced from said first process head and having a rigid knife blade engaging said moving web to extract excess polymer composition therefrom.

17. Apparatus as set forth in claim 1 including:

means for measuring micro porosity of the web before and after the processing zone; and means responsive to micro porosity measurements for controlling one or more of said shear thinning means, said tension applying means, said means for selectively positioning said knife blade and said polymer applying means.

18. Apparatus as set forth in claim 1 including:

means for measuring density of the web before and after the processing zone; and means responsive to web density measurements for controlling one or more of said shear thinning means, said tension applying means, said means for selectively positioning said knife blade and said polymer applying means.

19. Apparatus as set forth in claim 1 including:

means for analyzing the elements on an untreated side of the web after curing; and means responsive to an elemental analysis for controlling one or more of said shear thinning means, said tension applying means, said polymer applying means and said means for selectively positioning said knife blade.

20. Apparatus as set forth in claim 1 wherein said shear thinning means places an internal layer within said web; and said apparatus includes:

means for measuring placement of the internal layer; and means responsive to said measuring means for controlling one or more of said shear thinning means, said tension applying means, said polymer applying means, and said means for selectively positioning said knife blade to adjust the placement of said internal layer within said web.

21. Apparatus as set forth in claim 1 wherein said curing means includes a plurality of heating zones wherein a first zone includes means for infrared heating of the treated surface of the web and successive zones include means for convection and/or radiant heating of the treated web.

22. Apparatus as set forth in claim 1 wherein longitudinal tension of the web is substantially released immediately prior to curing.

23. Apparatus as set forth in claim 1 wherein said shear thinning means selectively places said polymer composition to encapsulate at least some of the structural elements of said web and to form an internal layer within said web.

24. Apparatus as set forth in claim 1 including means for spraying additives onto the treated web before curing.

25. Apparatus as set forth in claim 24 wherein said additives are pressured into said web before curing.

26. Apparatus as set forth in claim 1 including:

means for sensing a plurality of parameters selected from the group consisting of: the tension at one or more places within the processing zone, the positioning of said knife blade relative to said moving web, micro porosity of the moving web before and after the processing zone, the placement of an internal layer of polymer within said web, web density before and after the processing zone, an elemental analysis of the web after the processing zone, and an amount of polymer composition applied to the moving web; and means responsive to said measuring means for controlling one or more of said shear thinning means, said tension applying means, and said polymer applying means to adjust the placement of said internal layer within said web.

27. Apparatus as set forth in claim 1 including:

means for sensing a plurality of parameters selected from the group consisting of: the tension at one or more places within the processing zone, the position of said knife blade relative to said moving web, micro porosity of the moving web before and after the processing zone, the placement of an internal layer of polymer within said web, web density before and after the processing zone, an elemental analysis of the web after the processing zone, and the amount of polymer composition applied to the moving web; and online means for comparing selected parameters sensed by sensing means to preset ranges of parameters for a predetermined product to be made and for controlling one or more of said tension applying means, said polymer applying means and said shear thinning means in response to any selected parameter being outside of the range for the predetermined product.

* * * * *